United States Patent
Wang et al.

(10) Patent No.: US 10,300,483 B2
(45) Date of Patent: May 28, 2019

(54) MULTI-INDEX DETECTION MICROFLUIDIC CHIP AND METHODS OF USE

(71) Applicants: CapitalBio Corporation, Beijing (CN); Tsinghua University, Beijing (CN)

(72) Inventors: Lei Wang, Beijing (CN); Guohao Zhang, Beijing (CN); Xinying Zhou, Beijing (CN); Juan Xin, Beijing (CN); Yao Zhang, Beijing (CN); Mingxian Lin, Beijing (CN); Guoliang Huang, Beijing (CN); Can Wang, Beijing (CN); Wanli Xing, Beijing (CN); Jing Cheng, Beijing (CN)

(73) Assignee: Capitalbio Technology Corporation, Beijing (CN)

( * ) Notice: Subject to any disclaimer, the term of this patent is extended or adjusted under 35 U.S.C. 154(b) by 89 days.

(21) Appl. No.: 15/123,978

(22) PCT Filed: Mar. 6, 2015

(86) PCT No.: PCT/CN2015/000141
§ 371 (c)(1),
(2) Date: Sep. 6, 2016

(87) PCT Pub. No.: WO2015/131662
PCT Pub. Date: Sep. 11, 2015

(65) Prior Publication Data
US 2017/0014818 A1    Jan. 19, 2017

(30) Foreign Application Priority Data

Mar. 7, 2014   (CN) .......................... 2014 1 0082166

(51) Int. Cl.
*B01L 99/00*    (2010.01)
*B01L 3/00*    (2006.01)
*C12Q 1/6869*    (2018.01)

(52) U.S. Cl.
CPC .......... *B01L 3/5027* (2013.01); *C12Q 1/6869* (2013.01); *B01L 2200/025* (2013.01);
(Continued)

(58) Field of Classification Search
CPC ............................................... B01L 2300/0803
See application file for complete search history.

(56) References Cited

U.S. PATENT DOCUMENTS

| | | | |
|---|---|---|---|
| 2002/0047003 | A1 | 4/2002 | Bedingham et al. |
| 2002/0142481 | A1 | 10/2002 | Andersson et al. |

(Continued)

FOREIGN PATENT DOCUMENTS

| | | |
|---|---|---|
| CN | 101 609 088 | 12/2009 |
| CN | 102 369 443 | 3/2012 |

(Continued)

OTHER PUBLICATIONS

Extended European Search Report for EP 1 575 859.6, dated Sep. 22, 2017, 11 pages.

(Continued)

*Primary Examiner* — Paul S Hyun
(74) *Attorney, Agent, or Firm* — Rimon, P.C.

(57) ABSTRACT

A multi-index detection microfluidic chip is provided. A bottom plate (1) and a cover plate (2) that matches the bottom plate (1) and seals it are provided in the microfluidic chip. The center of the microfluidic chip has a through-hole (3). The bottom plate (1) has one or more wave-shaped main channel(s) (4), one end of each of the main channel (4) connected to a sample injection hole (9) on the bottom plate (1), and the other end connected to an exhaust hole (10) on the bottom plate (1). The valley on the main channel (1) is distal to the through-hole (3), and the peak is proximal to the through-hole (3). Each valley of the main channel (1) is connected to a reaction chamber (6) by a linking channel (5).

(Continued)

The linking channel (5) comprises one or more buffering chambers (7). The microfluidic chip can be used in detection by fluorescence, turbidity, color, detection equipment, and/or direct observation by the naked eyes. The detection is real-time as the reaction occurs or after the reaction.

32 Claims, 5 Drawing Sheets

(52) U.S. Cl.
CPC .................. *B01L 2200/0605* (2013.01); *B01L 2300/0803* (2013.01); *B01L 2300/087* (2013.01); *B01L 2300/0851* (2013.01); *B01L 2300/0864* (2013.01); *B01L 2300/0893* (2013.01); *B01L 2400/0409* (2013.01)

(56) References Cited

U.S. PATENT DOCUMENTS

| | | | |
|---|---|---|---|
| 2004/0120856 | A1 | 6/2004 | Andersson et al. |
| 2005/0199500 | A1 | 9/2005 | Gason et al. |
| 2009/0053108 | A1 | 2/2009 | Cho et al. |
| 2009/0308473 | A1 | 12/2009 | Shinoda et al. |
| 2009/0308746 | A1* | 12/2009 | Hwang ............. B01L 3/5085 204/407 |
| 2012/0015828 | A1 | 1/2012 | Ozawa et al. |
| 2014/0255933 | A1 | 9/2014 | Ozawa et al. |
| 2015/0217290 | A1 | 8/2015 | Zhang et al. |
| 2017/0014818 | A1 | 1/2017 | Wang et al. |

FOREIGN PATENT DOCUMENTS

| | | |
|---|---|---|
| CN | 103 055 973 | 4/2013 |
| CN | 103 831 140 | 6/2014 |
| EP | 2 028 496 | 2/2009 |
| EP | 2 484 748 | 8/2012 |
| JP | 2004-529333 | 9/2004 |
| JP | 2010-519892 | 6/2010 |
| JP | 2012-132935 | 7/2012 |
| JP | 2012-185000 | 9/2012 |
| WO | WO-2002/074438 | 1/2003 |
| WO | WO-2008/106719 | 9/2008 |
| WO | WO-2013/077391 | 5/2013 |
| WO | WO-2014/032396 | 3/2014 |

OTHER PUBLICATIONS

International Preliminary Report on Patentability for PCT/CN2015/000141, dated Jun. 1, 2015, 6 pages.
International Search Report and Written Opinion for PCT/CN2015/000141, dated Jun. 9, 2015, 10 pages.
Notice of Grounds of Rejection for JP 2016-572875, dated Sep. 26, 2017, 7 pages (Including English translation).
Response to Notice of Grounds of Rejection for JP 2016-572875, dated Dec. 25, 2017, 15 pages.
European Patent Office, Communication pursuant to Article 94(3) EPC for EP Application No. 15758596.9, dated Jul. 6, 2018, 6 pages.
European Patent Office, Communication pursuant to Rules 70(2) and 70a(2) EPC for Application No. EP 15758596.9, dated Oct. 10, 2017, 9 pages.
European Patent Office, Supplementary European Search Report for Application No. EP 15758596, dated Sep. 18, 2017, 3 pages.
State Intellectual Property Office for the People's Republic of China, Patent Search Report for Chinese Patent Application No. 2014100821662, dated Feb. 28, 2015, 2 pages.
Japan Patent Office, Final Decision for Rejection for Japanese Patent Application No. 2016-572875, dated Feb. 13, 2018, 13 pages.
European Patent Office, Response to the Communication pursuant to Rules 70(2) and 70a(2) EPC for Application No. EP 15758596.9, dated Apr. 20, 2018, 13 pages.
JP, Report of Reconsideration by Examiner before Appeal for Japanese Patent Application No. 2016-572875, dated Aug. 27, 2018, 2 pages, with English translation 2 pages.
JP, Written Amendment for Japanese Patent Application No. 2016-572875, dated Jun. 12, 2018, 4 pages, with English translation 5 pages.
JP, Final decision for rejection for Japanese Patent Application No. 2016-572875, dated Feb. 2, 2018, 8 pages, with English translation 13 pages.

* cited by examiner

MULTI-INDEX DETECTION MICROFLUIDIC CHIP AND METHODS OF USE

CROSS-REFERENCE TO RELATED APPLICATION

The present application is a U.S. national phase of International Patent Application No. PCT/CN2015/000141, filed Mar. 6, 2015, which claims priority benefit to Chinese Patent Application No. 201410082166.2, filed on Mar. 7, 2014, now Chinese Patent No. CN 103831140 B published on Dec. 30, 2015, the disclosures of which are incorporated by reference herein in their entireties for all purposes.

TECHNICAL FIELD

The present disclosure generally relates to the fields of microfluidic chip and detection and analysis of biological molecules. In certain aspects, the present disclosure relates to a multi-index detection microfluidic chip and methods of use.

BACKGROUND

Microfluidic chip is a hotspot in the development of Micro Total Analysis Systems (μ-TAS). The microfluidic chip technology uses the microfluidic chip as an operating platform, in combination with biological, chemical, and/or drug screening technologies. Typically, the platform is capable of completing the majority of steps in a whole analytical process, including reagent loading, separation, reaction, and/or detection. In recent years, with the rapid development of bio-chip technology, microfluidic chips play more and more important roles in the area of life science, analytical chemistry, and medicine.

For high-efficiency, rapid, and high-throughput detection of samples, chips typically need to have multiple reaction chambers and an effective transmission mode which can convey the samples or reagents to the reaction chambers. In general, microfluidic chips deliver the sample to the internal wells, channels, or holes in the chips by using external forces such as electromagnetic force, centrifugal force, and so on.

CN 101609088 A discloses a transmission fluid device. Electric force is applied to charged droplets, and the electric force controls the micro particles to move to the respective branches of the microfluidic channel. However, this method requires complex equipment that generates the electric field applied to the chip. In addition, because the liquid needs to be first converted into droplets in the electric field and be conveyed as droplets to the designated area, this method reduces the processing speed of the sample.

CN 103055973 A illustrates a delivery device based on an electro osmotic pump, which can separate different charged analytes. In general, this method only applies to charged samples and not to biological samples and non-charged samples.

Therefore, there is a need for microfluidic chips and methods of using the chips for high throughput, high sensitivity, and high accuracy reagent delivery. There is a need to not only realize the accurate dosing of sample or reagent in each reaction volume, but also avoid cross-contamination between adjacent reaction volumes.

SUMMARY OF THE INVENTION

The summary is not intended to be used to limit the scope of the claimed subject matter. Other features, details, utilities, and advantages of the claimed subject matter will be apparent from the detailed description including those aspects disclosed in the accompanying drawings and in the appended claims.

In one aspect, provided herein is a microfluidic chip, comprising: (1) a bottom plate comprising: at least one wave-shaped main channel comprising at least one valley and at least one peak; at least one sample inlet port; at least one exhaust port; and at least one reaction chamber, wherein one end of said at least one wave-shaped main channel is connected to said at least one sample inlet port, and the other end is connected to said at least one exhaust port, wherein said at least one valley points away from the center of said bottom plate, and said at least one peak points toward the center of said bottom plate, and wherein said at least one valley of said main channel is connected to said at least one reaction chamber; and (2) a cover plate fittingly engaging said bottom plate.

In one embodiment, said bottom plate further comprises at least one linking channel, said linking channel connecting said at least one valley of said main channel to said at least one reaction chamber, and wherein said linking channel comprises one or more buffering chambers.

In any of the preceding embodiments, said bottom plate can further comprise a central through-hole. In one aspect, said bottom plate can further comprise an earmark. In one embodiment, said earmark is a notch located on the inner edge of said central through-hole.

In any of the preceding embodiments, said cover plate can comprise a central through-hole which aligns with said central through-hole of said bottom plate. In one aspect, said cover plate matches and seals said bottom plate.

In any of the preceding embodiments, said bottom plate can comprise a plurality of said reaction chambers for multi-index detection, wherein said wave-shaped main channel comprises a plurality of peaks and valleys, wherein each of at least about 1%, about 5%, about 10%, about 20%, about 30%, about 40%, about 50%, about 60%, about 70%, about 80%, about 90%, about 95%, or all of said plurality of valleys is connected to one or more of said reaction chambers. In one embodiment, each of said reaction chambers comprises a reagent for detecting a target in a sample. In one aspect, said reaction chambers comprise at least two reagents, each of which detects a different target.

In any of the preceding embodiments, the volume of said buffering chamber can be between about 0.2 to about 0.8 times of the volume of said reaction chamber.

In any of the preceding embodiments, the junction between said linking channel and said reaction chamber can be located substantially on the line between the center of said bottom plate and the center of said reaction chamber, as long as the linking channel is capable of transferring the sample from the main channel to a corresponding reaction chamber when the microfluidic chip is subjected to a centrifugal force.

In any of the preceding embodiments, said main channel can form at least one circle. In one aspect, said main channel forms a plurality of concentric circles on said bottom plate.

In any of the preceding embodiments, said bottom plate can comprise one or more wave-shaped main channels forming one or more circles on said bottom plate.

In any of the preceding embodiments, the volume of said reaction chamber can be between about 0.1 μL and about 5 μL.

In any of the preceding embodiments, the volume of any V-shaped portion of said main channel can be between about 1.2 and about 1.8 times of the volume of the reaction chamber connected to it.

In any of the preceding embodiments, the ratio between the narrowest and the widest cross sectional areas in said main channel can be between about 0.2 and about 1.

In any of the preceding embodiments, the ratio between the narrowest and the widest cross sectional areas in said main channel can be less than about 1, and wherein the cross sectional area of said peak can be smaller than that of said valley.

In any of the preceding embodiments, said bottom plate can comprise between about 5 and about 100 reaction chambers.

In any of the preceding embodiments, the thickness of said bottom plate can be between about 0.05 mm and about 1 mm or between about 1 mm and about 5 mm, the thickness of said cover plate can be between about 0.05 mm and about 1 mm or between about 1 mm and about 5 mm.

In any of the preceding embodiments, the depth of said main channel can be between about 40 µm and about 800 µm or between about 800 µm and 4 mm, the depth of said reaction chamber can be between about 40 µm and about 800 µm or between about 800 µm and 4 mm, the depth of said linking channel can be between about 40 µm and about 800 µm or between about 800 µm and 4 mm, and the depth of said buffering chamber can be between about 40 µm and about 800 µm or between about 800 µm and 4 mm.

In any of the preceding embodiments, said sample inlet port can be round, and the size of said sample inlet port can match the size of a standard tip head.

In another aspect, provided herein is a method of analyzing an analyte, comprising: 1) loading a sample into the main channel of the microfluidic chip of any of the preceding embodiments; 2) applying a centrifugal force to the microfluidic chip, thereby delivering the sample from the main channel to the reaction chamber; 3) performing a reaction of the sample in the reaction chamber; and 4) measuring an indicator of the reaction, wherein the indicator indicates the presence, absence, amount, and/or a property of an analyte in the sample.

In yet another aspect, provided herein is a kit, comprising: the microfluidic chip of any of the preceding embodiments; and one or more reagents for performing a reaction in the microfluidic chip. In one aspect, the kit further comprises a reference indicator of the reaction. In one embodiment, the reference indicator comprises a positive and/or a negative reference indicator of the reaction. In another embodiment, the kit further comprises an instruction for interpreting a result of the reaction. In any of the preceding embodiments, the reaction can be a biological reaction, a chemical reaction, an immune reaction, a nucleic acid amplification reaction, or a polynucleotide/polypeptide sequencing reaction.

BRIEF DESCRIPTION OF THE DRAWINGS

FIG. 9(a) shows the pipette tip cannot be inserted into the sample inlet port, thereby causing leakage when loading the sample. FIG. 9(b) shows the pipette tip is fully inserted into the sample inlet port, thereby causing the tip head to touch the bottom of the chip and block loading of the sample. FIG. 9(c) shows that after the pipette tip is inserted into the sample inlet port, there is a gap between the tip head and the bottom of the chip, thereby allowing accurate loading of the sample without obstruction.

FIG. 12(a) shows 12 repeat test results with 1000 copies/µL Mtb (*Mycobacterium tuberculosis* complex) preparation. FIG. 12(b) shows test results of a clinical sample showing that there were Spn (*Streptococcus pneumoniae*) bacteria in the sample. FIG. 12(c) shows test results of a preparation mixture containing 7 types of bacteria each in a final concentration of 2000 copies/µL. FIG. 12(d) shows test results of a preparation mixture of Sau/Eco/Kpn each in a final concentration of 100 copies/µL, after the PathoDisc was stored at −20° C. for 11 months.

DETAILED DESCRIPTION OF EXEMPLARY EMBODIMENTS

Figure 1:
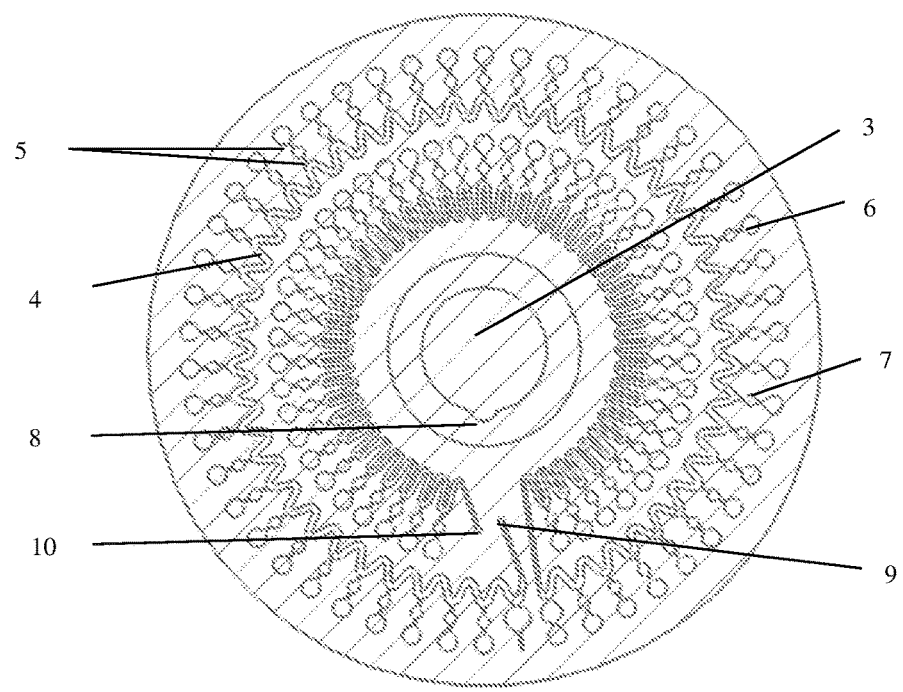
FIG. 1 is an aerial view of a microfluidic chip according to one aspect of the present disclosure. 1—Bottom plate; 2—Cover plate; 3—Through-hole; 4—Main channel; 5—Linking channel; 6—Reaction chamber; 7—Buffering chamber; 8—Earmark notch; 9—Sample inlet port; and 10—Exhaust port.

A detailed description of one or more embodiments of the claimed subject matter is provided below along with accompanying figures that illustrate the principles of the claimed subject matter. The claimed subject matter is described in connection with such embodiments, but is not limited to any particular embodiment. It is to be understood that the claimed subject matter may be embodied in various forms, and encompasses numerous alternatives, modifications and equivalents. Therefore, specific details disclosed herein are not to be interpreted as limiting, but rather as a basis for the claims and as a representative basis for teaching one skilled in the art to employ the claimed subject matter in virtually any appropriately detailed system, structure, or manner. Numerous specific details are set forth in the following description in order to provide a thorough understanding of the present disclosure. These details are provided for the purpose of example and the claimed subject matter may be practiced according to the claims without some or all of these specific details. It is to be understood that other embodiments can be used and structural changes can be made without departing from the scope of the claimed subject matter. It should be understood that the various features and functionality described in one or more of the individual embodiments are not limited in their applicability to the particular embodiment with which they are described. They instead can, be applied, alone or in some combination, to one or more of the other embodiments of the disclosure, whether or not such embodiments are described, and whether or not such features are presented as being a part of a described embodiment. For the purpose of clarity, technical material that is known in the technical fields related to the claimed subject matter has not been described in detail so that the claimed subject matter is not unnecessarily obscured.

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art.

All publications, including patent documents, scientific articles and databases, referred to in this application are incorporated by reference in their entireties for all purposes to the same extent as if each individual publication were individually incorporated by reference. If a definition set forth herein is contrary to or otherwise inconsistent with a definition set forth in the patents, patent applications, published applications or other publications that are herein incorporated by reference, the definition set forth herein prevails over the definition that is incorporated herein by reference. Citation of the publications or documents is not intended as an admission that any of them is pertinent prior art, nor does it constitute any admission as to the contents or date of these publications or documents.

All headings are for the convenience of the reader and should not be used to limit the meaning of the text that follows the heading, unless so specified.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

The practice of the provided embodiments will employ, unless otherwise indicated, conventional techniques and descriptions of organic chemistry, polymer technology, molecular biology (including recombinant techniques), cell biology, biochemistry, and sequencing technology, which are within the skill of those who practice in the art. Such conventional techniques include polypeptide and protein synthesis and modification, polynucleotide synthesis and modification, polymer array synthesis, hybridization and ligation of polynucleotides, and detection of hybridization using a label. Specific illustrations of suitable techniques can be had by reference to the examples herein. However, other equivalent conventional procedures can, of course, also be used. Such conventional techniques and descriptions can be found in standard laboratory manuals such as Green, et al., Eds., *Genome Analysis: A Laboratory Manual Series* (Vols. I-IV) (1999); Weiner, Gabriel, Stephens, Eds., *Genetic Variation: A Laboratory Manual* (2007); Dieffenbach, Dveksler, Eds., *PCR Primer: A Laboratory Manual* (2003); Bowtell and Sambrook, *DNA Microarrays: A Molecular Cloning Manual* (2003); Mount, *Bioinformatics: Sequence and Genome Analysis* (2004); Sambrook and Russell, *Condensed Protocols from Molecular Cloning: A Laboratory Manual* (2006); and Sambrook and Russell, *Molecular Cloning: A Laboratory Manual* (2002) (all from Cold Spring Harbor Laboratory Press); Ausubel et al. eds., *Current Protocols in Molecular Biology* (1987); T. Brown ed., *Essential Molecular Biology* (1991), IRL Press; Goeddel ed., *Gene Expression Technology* (1991), Academic Press; A. Bothwell et al. eds., *Methods for Cloning and Analysis of Eukaryotic Genes* (1990), Bartlett Publ.; M. Kriegler, *Gene Transfer and Expression* (1990), Stockton Press; R. Wu et al. eds., *Recombinant DNA Methodology* (1989), Academic Press; M. McPherson et al., *PCR: A Practical Approach* (1991), IRL Press at Oxford University Press; Stryer, *Biochemistry* (4th Ed.) (1995), W. H. Freeman, New York N.Y.; Gait, *Oligonucleotide Synthesis: A Practical Approach* (2002), IRL Press, London; Nelson and Cox, *Lehninger, Principles of Biochemistry* (2000) 3rd Ed., W. H. Freeman Pub., New York, N.Y.; Berg, et al., *Biochemistry* (2002) 5th Ed., W. H. Freeman Pub., New York, N.Y.; D. Weir & C. Blackwell, eds., *Handbook of Experimental Immunology* (1996), Wiley-Blackwell; A. Abbas et al., *Cellular and Molecular Immunology* (1991, 1994), W.B. Saunders Co.; and J. Coligan et al. eds., *Current Protocols in Immunology* (1991), all of which are herein incorporated in their entireties by reference for all purposes.

A. Definitions

As used herein and in the appended claims, the singular forms "a," "an," and "the" include plural referents unless the context clearly dictates otherwise. For example, "a" or "an" means "at least one" or "one or more." Thus, reference to "a reagent" refers to one or more reagents, and reference to "the method" includes reference to equivalent steps and methods disclosed herein and/or known to those skilled in the art, and so forth.

As used herein, the term "microfluidic device" generally refers to a device through which materials, particularly fluid borne materials, such as liquids, can be transported, in some embodiments on a micro-scale, and in some embodiments on a nanoscale. Thus, the microfluidic devices described by the presently disclosed subject matter can comprise microscale features, nanoscale features, and combinations thereof.

Accordingly, an exemplary microfluidic device typically comprises structural or functional features dimensioned on the order of a millimeter-scale or less, which are capable of manipulating a fluid at a flow rate on the order of a μL/min or less. Typically, such features include, but are not limited to, channels, fluid reservoirs, reaction chambers, mixing chambers, and separation regions. In some examples, the channels include at least one cross-sectional dimension that is in a range of from about 0.1 μm to about 500 μm. The use of dimensions on this order allows the incorporation of a greater number of channels in a smaller area, and utilizes smaller volumes of fluids.

A microfluidic device can exist alone or can be a part of a microfluidic system which, for example and without limitation, can include: pumps for introducing fluids, e.g., samples, reagents, buffers and the like, into the system and/or through the system; detection equipment or systems; data storage systems; and control systems for controlling fluid transport and/or direction within the device, monitoring and controlling environmental conditions to which fluids in the device are subjected, e.g., temperature, current, and the like.

As used herein, the terms "channel," "micro-channel," "fluidic channel," and "microfluidic channel" are used interchangeably and can mean a recess or cavity formed in a material by imparting a pattern from a patterned substrate into a material or by any suitable material removing technique, or can mean a recess or cavity in combination with any suitable fluid-conducting structure mounted in the recess or cavity, such as a tube, capillary, or the like. In the present invention, channel size means the cross-sectional area of the microfluidic channel.

As used herein, the terms "flow channel" and "control channel" are used interchangeably and can mean a channel in a microfluidic device in which a material, such as a fluid, e.g., a gas or a liquid, can flow through. More particularly, the term "flow channel" refers to a channel in which a material of interest, e.g., a solvent or a chemical reagent, can flow through. Further, the term "control channel" refers to a flow channel in which a material, such as a fluid, e.g., a gas or a liquid, can flow through in such a way to actuate a valve or pump.

As used herein, "chip" refers to a solid substrate with a plurality of one-, two- or three-dimensional micro structures or micro-scale structures on which certain processes, such as physical, chemical, biological, biophysical or biochemical processes, etc., can be carried out. The micro structures or micro-scale structures such as, channels and wells, electrode elements, electromagnetic elements, are incorporated into, fabricated on or otherwise attached to the substrate for facilitating physical, biophysical, biological, biochemical, chemical reactions or processes on the chip. The chip may be thin in one dimension and may have various shapes in other dimensions, for example, a rectangle, a circle, an ellipse, or other irregular shapes. The size of the major surface of chips of the present invention can vary considerably, e.g., from about 1 mm$^2$ to about 0.25 m$^2$. Preferably, the size of the chips is from about 4 mm$^2$ to about 25 cm$^2$ with a characteristic dimension from about 1 mm to about 5 cm. The chip surfaces may be flat, or not flat. The chips with non-flat surfaces may include channels or wells fabricated on the surfaces.

In one embodiment, the volumes of the reaction chambers on the same microfluidic chip are substantially identical. As used herein, "substantially identical" reaction volumes mean that the differences among the reaction volumes are sufficiently small not to statistically affect assay uniformity. Normally, the difference between the largest volume and the smallest volume is less than about 50% of the largest reaction volume. Preferably, the difference between the largest volume and the smallest volume is less than about 40%, about 30%, about 20%, about 10%, about 5%, about 2%, about 1%, about 0.5%, about 0.1%, about 0.01%, or less than about 0.001% of the largest reaction volume.

As used herein, a "sample" can be a solution, a suspension, liquid, powder, a paste, aqueous, non-aqueous or any combination thereof. A biological sample of the present disclosure encompasses a sample in the form of a solution, a suspension, a liquid, a powder, a paste, an aqueous sample, or a non-aqueous sample. As used herein, a "biological sample" includes any sample obtained from a living or viral (or prion) source or other source of macromolecules and biomolecules, and includes any cell type or tissue of a subject from which nucleic acid, protein and/or other macromolecule can be obtained. The biological sample can be a sample obtained directly from a biological source or a sample that is processed. For example, isolated nucleic acids that are amplified constitute a biological sample. Biological samples include, but are not limited to, body fluids, such as blood, plasma, serum, cerebrospinal fluid, synovial fluid, urine and sweat, tissue and organ samples from animals and plants and processed samples derived therefrom.

The terms "polynucleotide," "oligonucleotide," "nucleic acid" and "nucleic acid molecule" are used interchangeably herein to refer to a polymeric form of nucleotides of any length, and comprise ribonucleotides, deoxyribonucleotides, and analogs or mixtures thereof. The terms include triple-, double- and single-stranded deoxyribonucleic acid ("DNA"), as well as triple-, double- and single-stranded ribonucleic acid ("RNA"). It also includes modified, for example by alkylation, and/or by capping, and unmodified forms of the polynucleotide. More particularly, the terms "polynucleotide," "oligonucleotide," "nucleic acid," and "nucleic acid molecule" include polydeoxyribonucleotides (containing 2-deoxy-D-ribose), polyribonucleotides (containing D-ribose), including tRNA, rRNA, hRNA, and mRNA, whether spliced or unspliced, any other type of polynucleotide which is an N- or C-glycoside of a purine or pyrimidine base, and other polymers containing nonnucleotidic backbones, for example, polyamide (e.g., peptide nucleic acids ("PNAs")) and polymorpholino (commercially available from the Anti-Virals, Inc., Corvallis, Oreg., as Neugene) polymers, and other synthetic sequence-specific nucleic acid polymers providing that the polymers contain nucleobases in a configuration which allows for base pairing and base stacking, such as is found in DNA and RNA. Thus, these terms include, for example, 3'-deoxy-2',5'-DNA, oligodeoxyribonucleotide N3' to P5' phosphoramidates, 2'-O-alkyl-substituted RNA, hybrids between DNA and RNA or between PNAs and DNA or RNA, and also include known types of modifications, for example, labels, alkylation, "caps," substitution of one or more of the nucleotides with an analog, inter-nucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalkylphosphoramidates, aminoalkylphosphotriesters), those containing pendant moieties, such as, for example, proteins (including enzymes (e.g. nucleases), toxins, antibodies, signal peptides, poly-L-lysine, etc.), those with intercalators (e.g., acridine, psoralen, etc.), those containing chelates (of, e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide. A nucleic acid generally will contain phosphodiester bonds, although in some cases nucleic acid analogs may be included that have alternative backbones such as phosphoramidite, phosphorodithioate, or methylphophoroamidite linkages; or peptide nucleic acid backbones and linkages. Other analog nucleic acids include those with bicyclic structures including locked nucleic acids, positive backbones, non-ionic backbones and non-ribose backbones. Modifications of the ribose-phosphate backbone may be done to increase the stability of the molecules; for example, PNA:DNA hybrids can exhibit higher stability in some environments. The terms "polynucleotide," "oligonucleotide," "nucleic acid" and "nucleic acid molecule" can comprise any suitable length, such as at least 5, 6, 7, 8, 9, 10, 20, 30, 40, 50, 100, 200, 300, 400, 500, 1,000 or more nucleotides.

It will be appreciated that, as used herein, the terms "nucleoside" and "nucleotide" include those moieties which contain not only the known purine and pyrimidine bases, but also other heterocyclic bases which have been modified. Such modifications include methylated purines or pyrimidines, acylated purines or pyrimidines, or other heterocycles. Modified nucleosides or nucleotides can also include modifications on the sugar moiety, e.g., wherein one or more of the hydroxyl groups are replaced with halogen, aliphatic groups, or are functionalized as ethers, amines, or the like. The term "nucleotidic unit" is intended to encompass nucleosides and nucleotides.

The terms "polypeptide," "oligopeptide," "peptide," and "protein" are used interchangeably herein to refer to polymers of amino acids of any length, e.g., at least 5, 6, 7, 8, 9, 10, 20, 30, 40, 50, 100, 200, 300, 400, 500, 1,000 or more amino acids. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art.

The terms "binder," "binding agent," "binding moiety," and "binding group" as used herein refer to any agent or any moiety or group thereof that specifically binds to an analyte molecule of interest, e.g., a biological molecule or portions or complexes thereof with other molecules. In one embodiment, the reaction chamber of the microfluidic chip disclosed herein comprises a binder for one or more target molecules in the sample delivered to the reaction chamber. The binder can be immobilized, directly or indirectly, covalently or non-covalently, to the inner surface of the reaction chamber. The binder can be a polynucleotide (for example, a probe or an adaptor that hybridizes to a target polynucleotide, or an aptamer that can bind to pre-selected targets including proteins and peptides with high affinity and specificity) or a protein (for example, an antibody that specifically recognizes an epitope on a target protein).

An analyte that can be detected and/or analyzed using the chip disclosed herein can be any biological molecules including but not limited to proteins, nucleic acids, lipids, carbohydrates, ions, or multicomponent complexes containing any of the above. Examples of subcellular analytes of interest include organelles, e.g., mitochondria, Golgi apparatus, endoplasmic reticulum, chloroplasts, endocytic vesicles, exocytic vesicles, vacuoles, lysosomes, etc. Exemplary nucleic acid analyte can include genomic DNA of various conformations (e.g., A-DNA, B-DNA, Z-DNA), mitochondria DNA (mtDNA), mRNA, tRNA, rRNA, hRNA, miRNA, and piRNA.

As used herein, the term "binding" refers to an attractive interaction between two molecules which results in a stable association in which the molecules are in close proximity to each other. Molecular binding can be classified into the following types: non-covalent, reversible covalent and irreversible covalent. Molecules that can participate in molecular binding include proteins, nucleic acids, carbohydrates, lipids, and small organic molecules such as pharmaceutical compounds. For example, proteins that form stable complexes with other molecules are often referred to as receptors while their binding partners are called ligands. Nucleic acids can also form stable complex with themselves or others, for example, DNA-protein complex, DNA-DNA complex, DNA-RNA complex.

As used herein, the term "specific binding" refers to the specificity of a binder, e.g., an antibody, such that it preferentially binds to a target, such as a polypeptide antigen. When referring to a binding partner, e.g., protein, nucleic acid, antibody or other affinity capture agent, etc., "specific binding" can include a binding reaction of two or more binding partners with high affinity and/or complementarity to ensure selective hybridization under designated assay conditions. Typically, specific binding will be at least three times the standard deviation of the background signal. Thus, under designated conditions the binding partner binds to its particular target molecule and does not bind in a significant amount to other molecules present in the sample. Recognition by a binder or an antibody of a particular target in the presence of other potential interfering substances is one characteristic of such binding. Preferably, binders, antibodies or antibody fragments that are specific for or bind specifically to a target bind to the target with higher affinity than binding to other non-target substances. Also preferably, binders, antibodies or antibody fragments that are specific for or bind specifically to a target avoid binding to a significant percentage of non-target substances, e.g., non-target substances present in a testing sample. In some embodiments, binders, antibodies or antibody fragments of the present disclosure avoid binding greater than about 90% of non-target substances, although higher percentages are clearly contemplated and preferred. For example, binders, antibodies or antibody fragments of the present disclosure avoid binding about 91%, about 92%, about 93%, about 94%, about 95%, about 96%, about 97%, about 98%, about 99%, and about 99% or more of non-target substances. In other embodiments, binders, antibodies or antibody fragments of the present disclosure avoid binding greater than about 10%, 20%, 30%, 40%, 50%, 60%, or 70%, or greater than about 75%, or greater than about 80%, or greater than about 85% of non-target substances.

The terms "capture agent" and "capture group" as used herein refer to any moiety that allows capture of an analyte via binding to or linkage with an affinity group or domain on the analyte. The binding between the capture agent and its affinity tag may be a covalent bond and/or a non-covalent bond. A capture agent includes, e.g., a member of a binding pair that selectively binds to an affinity tag on a fusion peptide, a chemical linkage that is added by recombinant technology or other mechanisms, co-factors for enzymes and the like. Capture agents can be associated with a chip of the present disclosure (for example, the capture agent can be located in one or more of the reaction chambers) using conventional techniques including hybridization, cross-linking (e.g., covalent immobilization using a furocoumarin such as psoralen), attachment via chemically-reactive groups, and the like.

The term "antibody" as used herein includes an entire immunoglobulin or antibody or any functional fragment of an immunoglobulin molecule which is capable of specific binding to an antigen, such as a carbohydrate, polynucleotide, lipid, polypeptide, or a small molecule, etc., through at least one antigen recognition site, located in the variable region of the immunoglobulin molecule, and can be an immunoglobulin of any class, e.g., IgG, IgM, IgA, IgD and IgE. IgY, which is the major antibody type in avian species such as chicken, is also included. Secreted antibodies can be dimeric with two Ig units as with IgA, tetrameric with four Ig units like teleost fish IgM, or pentameric with five Ig units, like mammalian IgM.

An antibody includes the entire antibody as well as any antibody fragments capable of binding the antigen or antigenic fragment, for example, an epitope, of interest. Examples include complete antibody molecules, antibody fragments or linked antibody fragments, such as Fab, F(ab')$_2$, chemically linked F(ab')$_2$, Fab', scFv (single-chain variable fragment), di-scFv, sdAb (single domain antibody), trifunctional antibody, BiTE (bi-specific T-cell engager), CDRs, $V_L$, $V_H$, and any other portion of an antibody which is capable of specifically binding to an antigen. Antibodies used herein are immunoreactive or immunospecific for, and therefore specifically and selectively bind to, for example, proteins either detected (i.e., analytes in biological samples) or used for detection (i.e., binders or probes) in the assays disclosed herein. An antibody as used herein can be specific for any of the analytes, binders, or epitopes disclosed herein or any combinations thereof. In certain embodiments, an analyte itself of the present disclosure can be an antibody or fragments thereof.

As used herein, the term "antigen" may refer to a target molecule that is specifically bound by an antibody through its antigen recognition site. The antigen may be monovalent or polyvalent, i.e., it may have one or more epitopes recognized by one or more antibodies. Examples of kinds of antigens that can be recognized by antibodies include polypeptides, oligosaccharides, glycoproteins, polynucleotides, lipids, or small molecules, etc.

As used herein, the term "epitope" can refer to a peptide sequence of at least about 3 to 5, preferably about 5 to 10 or 15, and not more than about 1,000 amino acids (or any integer there between), which define a sequence that by itself or as part of a larger sequence, binds to an antibody generated in response to such sequence. There is no critical upper limit to the length of the fragment, which may, for example, comprise nearly the full-length of the antigen sequence, or even a fusion protein comprising two or more epitopes from the target antigen. An epitope for use in the present disclosure is not limited to a peptide having the exact sequence of the portion of the parent protein from which it is derived, but also encompasses sequences identical to the native sequence, as well as modifications to the native sequence, such as deletions, additions and substitutions (conservative in nature).

The terms "complementary" and "substantially complementary" include the hybridization or base pairing or the formation of a duplex between nucleotides or nucleic acids, for instance, between the two strands of a double-stranded DNA molecule or between an oligonucleotide primer and a primer binding site on a single-stranded nucleic acid. Complementary nucleotides are, generally, A and T (or A and U), or C and G. Two single-stranded RNA or DNA molecules are said to be substantially complementary when the nucleotides of one strand, optimally aligned and compared and with appropriate nucleotide insertions or deletions, pair with at least about 80% of the other strand, usually at least about 90% to about 95%, and even about 98% to about 100%. In one aspect, two complementary sequences of nucleotides are capable of hybridizing, preferably with less than 25%, more preferably with less than 15%, even more preferably with less than 5%, most preferably with no mismatches between opposed nucleotides. Preferably the two molecules will hybridize under conditions of high stringency.

"Hybridization" as used herein may refer to the process in which two single-stranded polynucleotides bind non-covalently to form a stable double-stranded polynucleotide. In one aspect, the resulting double-stranded polynucleotide can be a "hybrid" or "duplex." "Hybridization conditions" typically include salt concentrations of approximately less than 1 M, often less than about 500 mM and may be less than about 200 mM. A "hybridization buffer" includes a buffered salt solution such as 5% SSPE, or other such buffers known in the art. Hybridization temperatures can be as low as 5° C., but are typically greater than 22° C., and more typically greater than about 30° C., and typically in excess of 37° C. Hybridizations are often performed under stringent conditions, i.e., conditions under which a sequence will hybridize to its target sequence but will not hybridize to other, non-complementary sequences. Stringent conditions are sequence-dependent and are different in different circumstances. For example, longer fragments may require higher hybridization temperatures for specific hybridization than short fragments. As other factors may affect the stringency of hybridization, including base composition and length of the complementary strands, presence of organic solvents, and the extent of base mismatching, the combination of parameters is more important than the absolute measure of any one parameter alone. Generally stringent conditions are selected to be about 5° C. lower than the $T_m$ for the specific sequence at a defined ionic strength and pH. The melting temperature $T_m$ can be the temperature at which a population of double-stranded nucleic acid molecules becomes half dissociated into single strands. Several equations for calculating the $T_m$ of nucleic acids are well known in the art. As indicated by standard references, a simple estimate of the $T_m$ value may be calculated by the equation, $T_m=81.5+0.41$ (% G+C), when a nucleic acid is in aqueous solution at 1 M NaCl (see e.g., Anderson and Young, Quantitative Filter Hybridization, in *Nucleic Acid Hybridization* (1985)). Other references (e.g., Allawi and SantaLucia, Jr., *Biochemistry*, 36:10581-94 (1997)) include alternative methods of computation which take structural and environmental, as well as sequence characteristics into account for the calculation of $T_m$.

In general, the stability of a hybrid is a function of the ion concentration and temperature. Typically, a hybridization reaction is performed under conditions of lower stringency, followed by washes of varying, but higher, stringency. Exemplary stringent conditions include a salt concentration of at least 0.01 M to no more than 1 M sodium ion concentration (or other salt) at a pH of about 7.0 to about 8.3 and a temperature of at least 25° C. For example, conditions of 5×SSPE (750 mM NaCl, 50 mM sodium phosphate, 5 mM EDTA at pH 7.4) and a temperature of approximately 30° C. are suitable for allele-specific hybridizations, though a suitable temperature depends on the length and/or GC content of the region hybridized. In one aspect, "stringency of hybridization" in determining percentage mismatch can be as follows: 1) high stringency: 0.1×SSPE, 0.1% SDS, 65° C.; 2) medium stringency: 0.2×SSPE, 0.1% SDS, 50° C. (also referred to as moderate stringency); and 3) low stringency: 1.0×SSPE, 0.1% SDS, 50° C. It is understood that equivalent stringencies may be achieved using alternative buffers, salts and temperatures. For example, moderately stringent hybridization can refer to conditions that permit a nucleic acid molecule such as a probe to bind a complementary nucleic acid molecule. The hybridized nucleic acid molecules generally have at least 60% identity, including for example at least any of 70%, 75%, 80%, 85%, 90%, or 95% identity. Moderately stringent conditions can be conditions equivalent to hybridization in 50% formamide, 5×Denhardt's solution, 5×SSPE, 0.2% SDS at 42° C., followed by washing in 0.2×SSPE, 0.2% SDS, at 42° C. High stringency conditions can be provided, for example, by hybridization in 50% formamide, 5×Denhardt's solution, 5×SSPE, 0.2% SDS at 42° C., followed by washing in 0.1×SSPE, and 0.1% SDS at 65° C. Low stringency hybridization can refer to conditions equivalent to hybridization in 10% formamide, 5×Denhardt's solution, 6×SSPE, 0.2% SDS at 22° C., followed by washing in 1×SSPE, 0.2% SDS, at 37° C. Denhardt's solution contains 1% Ficoll, 1% polyvinylpyrolidone, and 1% bovine serum albumin (BSA). 20×SSPE (sodium chloride, sodium phosphate, EDTA) contains 3 M sodium chloride, 0.2 M sodium phosphate, and 0.025 M EDTA. Other suitable moderate stringency and high stringency hybridization buffers and conditions are well known to those of skill in the art and are described, for example, in Sambrook et al., Molecular Cloning: A Laboratory Manual, 2nd ed., Cold Spring Harbor Press, Plainview, N.Y. (1989); and Ausubel et al., Short Protocols in Molecular Biology, 4th ed., John Wiley & Sons (1999).

Alternatively, substantial complementarity exists when an RNA or DNA strand will hybridize under selective hybridization conditions to its complement. Typically, selective hybridization will occur when there is at least about 65% complementary over a stretch of at least 14 to 25 nucleotides, preferably at least about 75%, more preferably at least about 90% complementary. See M. Kanehisa, Nucleic Acids Res. 12:203 (1984).

A "primer" used herein can be an oligonucleotide, either natural or synthetic, that is capable, upon forming a duplex with a polynucleotide template, of acting as a point of initiation of nucleic acid synthesis and being extended from its 3' end along the template so that an extended duplex is formed. The sequence of nucleotides added during the extension process is determined by the sequence of the template polynucleotide. Primers usually are extended by a polymerase, for example, a DNA polymerase.

A sequencing reaction and the like include determination of information relating to the nucleotide base sequence of a nucleic acid. Such information may include the identification or determination of partial as well as full sequence information of the nucleic acid. Sequence information may be determined with varying degrees of statistical reliability or confidence. In one aspect, the term includes the determination of the identity and ordering of a plurality of contiguous nucleotides in a nucleic acid. "High throughput sequencing" or "next generation sequencing" includes sequence determination using methods that determine many (typically thousands to billions) of nucleic acid sequences in an intrinsically parallel manner, i.e. where DNA templates are prepared for sequencing not one at a time, but in a bulk process, and where many sequences are read out preferably in parallel, or alternatively using an ultra-high throughput serial process that itself may be parallelized. Such methods include but are not limited to pyrosequencing (for example, as commercialized by 454 Life Sciences, Inc., Branford, Conn.); sequencing by ligation (for example, as commercialized in the SOLiD™ technology, Life Technologies, Inc., Carlsbad, Calif.); sequencing by synthesis using modified nucleotides (such as commercialized in TruSeq™ and HiSeg™ technology by Illumina, Inc., San Diego, Calif.; HeliScope™ by Helicos Biosciences Corporation, Cambridge, Mass.; and PacBio RS by Pacific Biosciences of California, Inc., Menlo Park, Calif.), sequencing by ion detection technologies (such as Ion Torrent™ technology, Life Technologies, Carlsbad, Calif.); sequencing of DNA nanoballs (Complete Genomics, Inc., Mountain View, Calif.); nanopore-based sequencing technologies (for example, as developed by Oxford Nanopore Technologies, LTD, Oxford, UK), and like highly parallelized sequencing methods.

"Multiplexing," "multiplex assay," or "multi-index assay" herein may refer to an assay or other analytical method in which the presence and/or amount of multiple targets, e.g., multiple nucleic acid sequences, can be assayed simultaneously, for example, by using more than one capture probe conjugate, each of which has at least one different detection characteristic, e.g., fluorescence characteristic (for example excitation wavelength, emission wavelength, emission intensity, FWHM (full width at half maximum peak height), or fluorescence lifetime) or a unique nucleic acid or protein sequence characteristic.

It is understood that aspects and embodiments of the invention described herein include "consisting" and/or "consisting essentially of" aspects and embodiments.

B. Microfluidic Chips and Microfluidic Systems

In one aspect, the present disclosure provides a multi-index detection microfluidic chip. In one embodiment, the microfluidic chip adopts centrifugation for uniformly distributing samples into reaction chambers, in which one or more targets are detected and/or assayed. In one aspect, the present disclosure achieves uniform distribution of the samples by using a suitable ratio of cross-sectional areas of the main channel. In one aspect, the ratio of cross-sectional areas of the main channel can be adjusted to achieve optimal uniform distribution of the samples into the reaction chambers. In another aspect, the present disclosure ensures that the reaction chambers are fully filled with a sample after centrifugal distribution, through the design of buffering chambers. In one aspect, the present disclosure ensures that the reaction chambers sustain a fully-filled state during the entire reaction period, and in specific embodiments, reduces or prevents the reaction product of each reaction chamber to spread to the main channel and adjacent reaction chambers.

In certain embodiments, the present disclosure provides a multi-index detection microfluidic chip, comprising a bottom plate and a cover plate that matches the bottom plate and seals it. In one aspect, the center of the microfluidic chip has a through-hole.

In some aspects, the bottom plate comprises an exterior portion or surface, as well as an interior portion which defines the various microscale channels and/or chambers of the overall microfluidic device. For example, the body structure of an exemplary microfluidic devices typically employs a solid or semi-solid substrate that may be planar in structure, e.g., substantially flat or having at least one flat surface. Suitable substrates may be fabricated from any one of a variety of materials, or combinations of materials. Often, the planar substrates are manufactured using solid substrates common in the fields of microfabrication, e.g., silica-based substrates, such as glass, quartz, silicon or polysilicon, as well as other known substrates, e.g., gallium arsenide. In the case of these substrates, common microfabrication techniques, such as photolithographic techniques, wet chemical etching, micromachining, e.g., drilling, milling and the like, may be readily applied in the fabrication of microfluidic devices and substrates. Alternatively, polymeric substrate materials may be used to fabricate the devices of the present invention, including, e.g., polydimethylsiloxanes (PDMS), polymethylmethacrylate (PMMA), polyurethane, polyvinylchloride (PVC), polystyrene, polysulfone, polycarbonate and the like. In the case of such polymeric materials, injection molding or embossing methods may be used to form the substrates having the channel and reservoir geometries as described herein. In such cases, original molds may be fabricated using any of the above described materials and methods.

The channels and chambers of an exemplary device are typically fabricated into one surface of a planar substrate, as grooves, wells or depressions in that surface. A second planar substrate, typically prepared from the same or similar material, is overlaid and bound to the first, thereby defining and sealing the channels and/or chambers of the device. Together, the upper surface of the first substrate, and the lower mated surface of the upper substrate, define the interior portion of the device, i.e., defining the channels and chambers of the device. In some embodiments, the upper layer may be reversibly bound to the lower layer.

Exemplary systems may also include sample sources that are external to the body of the device per se, but still in fluid communication with the sample loading channel. In some embodiments, the system may further comprise an inlet and/or an outlet to the micro-channel. In some embodiments, the system may further comprise a delivering means to introduce a sample to the micro-channel. In some embodiments, the system may further comprise an injecting means to introduce a liquid into the micro-channel. Any liquid manipulating equipment, such as pipettes, pumps, etc., may be used as an injecting means to introduce a liquid to the micro-channel.

In certain embodiments, the bottom plate of the microfluidic chip has one or more wave-shaped main channels. In a particular aspect, one end of each of the main channel(s) connects to a sample inlet port (e.g., a hole for sample loading or injection), and the other end connects to an exhaust port (e.g., an exhaust hole). In some aspects, the sample inlet port or the exhaust port or both are on the bottom plate.

In one aspect, the valley of the wave-shaped main channel is distal to the through-hole, and the peak of the main channel is proximal to the through-hole. In another aspect, the valley of the main channel points away from the center of the bottom plate (for example, the through-hole in the center of the bottom plate), and the peak of the main channel points toward the center of the bottom plate (for example, the central through-hole). In some embodiments, the wave-shaped main channel comprises at least 1, 2, 3, 4, 5, 6, 7, 8, 9, or 10 valleys. In some embodiments, the wave-shaped main channel comprises at least about 10, about 20, about 40, about 60, about 80, about 100, about 120, about 140, about 160, about 180, or about 200 valleys. In some embodiments, the wave-shaped main channel comprises between about 200 and about 400, between about 400 and about 600, between about 600 and about 800, between about 800 and about 1000, or more than about 1000 valleys. In some embodiments, the wave-shaped main channel comprises at least 1, 2, 3, 4, 5, 6, 7, 8, 9, or 10 peaks. In some embodiments, the wave-shaped main channel comprises at least about 10, about 20, about 40, about 60, about 80, about 100, about 120, about 140, about 160, about 180, or about 200 peaks. In some embodiments, the wave-shaped main channel comprises between about 200 and about 400, between about 400 and about 600, between about 600 and about 800, between about 800 and about 1000, or more than about 1000 peaks. In some embodiments, the wave-shaped main channel comprises at least 1, 2, 3, 4, 5, 6, 7, 8, 9, or 10 valley/peak pairs (one peak and one valley adjacent and connected to each other). In some embodiments, the wave-shaped main channel comprises at least about 10, about 20, about 40, about 60, about 80, about 100, about 120, about 140, about 160, about 180, or about 200 valley/peak pairs. In some embodiments, the wave-shaped main channel comprises between about 200 and about 400, between about 400 and about 600, between about 600 and about 800, between about 800 and about 1000, or more than about 1000 valley/peak pairs. In any of the preceding embodiments, each of the valleys of the main channel can be connected to at least one reaction chamber via a linking channel on the bottom plate.

In one aspect, the linking channel comprises at least one buffering chamber, and the buffering chamber is located on the linking channel, between the reaction chamber and the main channel. In one aspect, the volume of the buffering chamber is between about 0.2 and about 0.8 times of the volume of the reaction chamber that it is connected to. In some aspects, the ratio between the volume of said buffering chamber and the volume of said reaction chamber is less than about 0.2, between about 0.2 and about 0.3, between about 0.3 and about 0.4, between about 0.4 and about 0.5, between about 0.5 and about 0.6, between about 0.6 and about 0.7, between about 0.7 and about 0.8, or more than about 0.8.

In another aspect, the junction between the linking channel and the reaction chamber is located in a line connecting the center of the microfluidic chip and the reaction chamber.

In one embodiment, in the bottom plate, the main channels are distributed in one or more circles. In another aspect, one or more main channels are formed by one or more circles.

In some embodiments, the volume of the reaction chamber is between about 0.1 µL and about 5.0 µL. In some embodiments, the volume of the reaction chamber is less than about 0.01 µL, between about 0.01 µL and about 0.05

μL, between about 0.05 μL and about 0.1 μL, between about 0.1 μL and about 0.2 μL, between about 0.1 μL and about 0.2 μL, between about 0.2 μL and about 0.3 μL, between about 0.3 μL and about 0.4 μL, between about 0.4 μL and about 0.5 μL, between about 0.5 μL and about 0.6 μL, between about 0.6 μL and about 0.7 μL, between about 0.7 μL and about 0.8 μL, between about 0.8 μL and about 0.9 μL, between about 0.9 μL and about 1.0 μL, between about 1.0 μL and about 1.1 μL, between about 1.1 μL and about 1.2 μL, between about 1.2 μL and about 1.3 μL, between about 1.3 μL and about 1.4 μL, between about 1.4 μL and about 1.5 μL, between about 1.5 μL and about 1.6 μL, between about 1.6 μL and about 1.7 μL, between about 1.7 μL and about 1.8 μL, between about 1.8 μL and about 1.9 μL, between about 1.9 μL and about 2.0 μL, between about 2.0 μL and about 2.1 μL, between about 2.1 μL and about 2.2 μL, between about 2.2 μL and about 2.3 μL, between about 2.3 μL and about 2.4 μL, between about 2.4 μL and about 2.5 μL, between about 2.5 μL and about 2.6 μL, between about 2.6 μL and about 2.7 μL, between about 2.7 μL and about 2.8 μL, between about 2.8 μL and about 2.9 μL, between about 2.9 μL and about 3.0 μL, between about 3.0 μL and about 3.1 μL, between about 3.1 μL and about 3.2 μL, between about 3.2 μL and about 3.3 μL, between about 3.3 μL and about 3.4 μL, between about 3.4 μL and about 3.5 μL, between about 3.5 μL and about 3.6 μL, between about 3.6 μL and about 3.7 μL, between about 3.7 μL and about 3.8 μL, between about 3.8 μL and about 3.9 μL, between about 3.9 μL and about 4.0 μL, between about 4.0 μL and about 4.1 μL, between about 4.1 μL and about 4.2 μL, between about 4.2 μL and about 4.3 μL, between about 4.3 μL and about 4.4 μL, between about 4.4 μL and about 4.5 μL, between about 4.5 μL and about 4.6 μL, between about 4.6 μL and about 4.7 μL, between about 4.7 μL and about 4.8 μL, between about 4.8 μL and about 4.9 μL, between about 4.9 μL and about 5.0 μL, or more than about 5.0 μL.

In particular embodiments, at least one or all of the reaction chambers of microfluidic chip are pre-loaded with a reagent that is capable of specific interaction and/or reaction with one or more components of the sample. In one aspect, the reagent comprises a nucleic acid, for example, a polynucleotide that is capable of specific hybridization with one or more target nucleic acids in the sample.

In some embodiments, the ratio between the volume of any V-shaped portion (the V-shaped portion comprising the valley) of the main channel and the volume of the reaction chamber connected to the valley is between about 1.2 and about 1.8, and in particular embodiments, the ratio is less than about 1.2, between about 1.2 and about 1.3, between about 1.3 and about 1.4, between about 1.4 and about 1.5, between about 1.5 and about 1.6, between about 1.6 and about 1.7, between about 1.7 and about 1.8, or more than about 1.8.

In some embodiments, the ratio between the narrowest and the widest cross sectional areas in the main channel is between about 0.2 and about 1, and in particular embodiments, the ratio is less than about 0.2, between about 0.2 and about 0.3, between about 0.3 and about 0.4, between about 0.4 and about 0.5, between about 0.5 and about 0.6, between about 0.6 and about 0.7, between about 0.7 and about 0.8, between about 0.8 and about 0.9, or between about 0.9 and about 1.0. In one aspect, where the ratio between the narrowest and the widest cross sectional areas in the main channel is less than about 1.0, the cross sectional area of the peak is smaller than that of the valley.

In any of the preceding embodiments, the microfluidic chip can comprise between about 5 and about 100 reaction chambers. In some embodiments, the microfluidic chip comprises at least 1, 2, 3, 4, 5, 6, 7, 8, 9, or 10 reaction chambers. In some embodiments, the microfluidic chip comprises at least about 10, about 20, about 40, about 60, about 80, about 100, about 120, about 140, about 160, about 180, or about 200 reaction chambers. In some embodiments, the microfluidic chip comprises between about 200 and about 400, between about 400 and about 600, between about 600 and about 800, between about 800 and about 1000, or more than about 1000 reaction chambers. The reaction chambers on the microfluidic chip can be divided into one or more groups. For example, reaction chambers connected to the same main channel can be grouped together, and the microfluidic chip can comprise more than one main channels and each main channel is connected to a distinct group of reaction chambers. In one aspect, reaction chambers of different groups are not connected.

In any of the preceding embodiments, the thickness of the bottom plate can be less than about 0.05 mm, between about 0.05 mm and about 1 mm, between about 1 mm and about 5 mm, or more than about 5 mm. In particular embodiments, the thickness of the bottom plate is between about 0.05 mm and about 0.1 mm, between about 0.1 mm and about 0.2 mm, between about 0.2 mm and about 0.3 mm, between about 0.3 mm and about 0.4 mm, between about 0.4 mm and about 0.5 mm, between about 0.5 mm and about 0.6 mm, between about 0.6 mm and about 0.7 mm, between about 0.7 mm and about 0.8 mm, between about 0.8 mm and about 0.9 mm, between about 0.9 mm and about 1.0 mm, between about 1.0 mm and about 1.5 mm, between about 1.5 mm and about 2.0 mm, between about 2.0 mm and about 2.5 mm, between about 2.5 mm and about 3.0 mm, between about 3.0 mm and about 3.5 mm, between about 3.5 mm and about 4.0 mm, between about 4.0 mm and about 4.5 mm, between about 4.5 mm and about 5.0 mm, or more than about 5.0 mm. In any of the preceding embodiments, the thickness of the cover plate can be less than about 0.05 mm, between about 0.05 mm and about 1 mm, or more than about 1 mm. In particular embodiments, the thickness of the cover plate is between about 0.05 mm and about 0.1 mm, between about 0.1 mm and about 0.2 mm, between about 0.2 mm and about 0.3 mm, between about 0.3 mm and about 0.4 mm, between about 0.4 mm and about 0.5 mm, between about 0.5 mm and about 0.6 mm, between about 0.6 mm and about 0.7 mm, between about 0.7 mm and about 0.8 mm, between about 0.8 mm and about 0.9 mm, between about 0.9 mm and about 1.0 mm, between about 1.0 mm and about 1.5 mm, between about 1.5 mm and about 2.0 mm, between about 2.0 mm and about 2.5 mm, between about 2.5 mm and about 3.0 mm, between about 3.0 mm and about 3.5 mm, between about 3.5 mm and about 4.0 mm, between about 4.0 mm and about 4.5 mm, between about 4.5 mm and about 5.0 mm, or more than about 5.0 mm.

In any of the preceding embodiments, the thickness of the cover plate or the bottom plate or both can be optimized. In one aspect, if the thickness is too thin, the cover plate and the bottom plate can be easily deformed. In another aspect, the depth of the channel can be affected by the thickness of the plates, and if the sheets are too thick, the amount of reagents that can be loaded into the chip will be reduced. In yet another aspect, if the thickness is too thick, the thermal properties of chip material will be affected, which can cause the nonuniform heating of the chip and thus affect the test results.

In any of the preceding embodiments, the depth of the main channel, the reaction chamber, the linking channel, and/or the buffering chamber can be less than about 40 μm, between about 40 μm and about 800 μm, between about 800

μm and about 1 mm, between about 1 mm and about 1.5 mm, between about 1.5 mm and about 2 mm, between about 2 mm and about 2.5 mm, between about 2.5 mm and about 3 mm, between about 3 mm and about 3.5 mm, between about 3.5 mm and about 4 mm, or more than about 4 mm. In particular embodiments, the depth of the main channel, the reaction chamber, the linking channel, and/or the buffering chamber is between about 40 μm and about 50 μm, between about 50 μm and about 60 μm, between about 60 μm and about 70 μm, between about 70 μm and about 80 μm, between about 80 μm and about 90 μm, between about 90 μm and about 100 μm, between about 100 μm and about 150 μm, between about 150 μm and about 200 μm, between about 200 μm and about 250 μm, between about 250 μm and about 300 μm, between about 300 μm and about 350 μm, between about 350 μm and about 400 μm, between about 400 μm and about 450 μm, between about 450 μm and about 500 μm, between about 500 μm and about 550 μm, between about 550 μm and about 600 μm, between about 600 μm and about 650 μm, between about 650 μm and about 700 μm, between about 700 μm and about 750 μm, or between about 750 μm and about 800 μm. In particular embodiments, the depth of the main channel, the reaction chamber, the linking channel, and/or the buffering chamber is between about 800 μm and about 900 μm, between about 900 μm and about 1.0 mm, between about 1.0 mm and about 1.1 mm, between about 1.1 mm and about 1.2 mm, between about 1.2 mm and about 1.3 mm, between about 1.3 mm and about 1.4 mm, between about 1.4 mm and about 1.5 mm, between about 1.5 mm and about 1.6 mm, between about 1.6 mm and about 1.7 mm, between about 1.7 mm and about 1.8 mm, between about 1.8 mm and about 1.9 mm, between about 1.9 mm and about 2.0 mm, between about 2.1 mm and about 2.2 mm, between about 2.2 mm and about 2.3 mm, between about 2.3 mm and about 2.4 mm, between about 2.4 mm and about 2.5 mm, between about 2.5 mm and about 2.6 mm, between about 2.6 mm and about 2.7 mm, between about 2.7 mm and about 2.8 mm, between about 2.8 mm and about 2.9 mm, between about 2.9 mm and about 3.0 mm, between about 3.1 mm and about 3.2 mm, between about 3.2 mm and about 3.3 mm, between about 3.3 mm and about 3.4 mm, between about 3.4 mm and about 3.5 mm, between about 3.5 mm and about 3.6 mm, between about 3.6 mm and about 3.7 mm, between about 3.7 mm and about 3.8 mm, between about 3.8 mm and about 3.9 mm, between about 3.9 mm and about 4.0 mm.

In any of the preceding embodiments, the sample inlet port (e.g., the sample injection hole) of the bottom plate can be an orifice, for example, an orifice that is circular or round in shape. In other embodiments, the orifice can be square, rectangular, circular, elliptical, oval, or of an irregular shape. In one aspect, the size of the orifice matches the dimensions of standard tip head in biological assays, such that operators can use the standard tip to inject samples directly into the sample injection hole. In one aspect, the design of the sample injection hole makes it easier to manufacture and/or use the microfluidic chip.

In any of the preceding embodiments, the inner edge of through-hole can be provided with a locating notch, which in one aspect plays the role of fixing the chip when the sample is distributed into the reaction chambers by centrifugal force. In another aspect, when the chip is used for analysis in an instrument, the locating notch plays the role in positioning and thus identifying each of the reaction chambers.

In any of the preceding embodiments, a double faced adhesive tape can be used to bond the bottom plate and the cover plate firmly. In one aspect, the double faced adhesive tape has the desired adhesive strength and resistance to conventional heating temperatures, and has no significant adverse effects on the specificity of the reactions in the chip.

In general, polymer microfluidic chip can be manufactured using heat pressing and/or laser welding to bond the bottom plate and the cover plate by heating and melting their surfaces. Heat pressing and laser welding, however, are relatively expensive. In the case of pre-loaded sample in the bottom of the chip, the process of laser welding and heat pressing can have a negative impact on biological activity and/or chemical property of the pre-loaded sample. In addition, these two processing methods may have an impact on the shape of the microfluidic channel, and can even cause channel blockage or chip leakage.

In the present disclosure, in one aspect, the double faced adhesive tapes have sufficient adhesive strength and capacity to withstand various heating conditions in biological assays. In one aspect, the double faced adhesive tapes prevent chip leakage in various heating conditions and thus prevent test failure or environmental contamination due to chip leakage.

In the present disclosure, in one aspect, the double faced adhesive tapes have appropriate biocompatibility, and can maintain the biological activities and chemical properties of the test samples, including embedded samples. In another aspect, the double faced adhesive tapes do not significantly or adversely affect the reaction in the chip, including the specificity of the reaction in the chip.

In the present disclosure, in one aspect, the double faced adhesive tapes have optical properties that are compatible with the detection means in the present disclosure. For example, when fluorescence detection are used to detect fluorescence that passes through, the double faced adhesive tape has sufficient optical transmittance for fluorescent light emitted from the reaction chambers. In another aspect, when fluorescence is to be detected by reflection, the fluorescence background of the double faced adhesive tape is low enough at the detection wavelengths to allow sensitive detection of fluorescent light emitted from the reaction chambers.

In one aspect, the chip of the disclosure uses a viscous sealing membrane to seal. In other aspects, the chip can be sealed using mineral oil or silicone oil through secondary loading in order to seal the initially loaded samples in the chip. Compared to using mineral oil or silicone oil, using a viscous sealing membrane to seal the chip avoids secondary loading and reduces the burden on the operator.

In one aspect, using a microfluidic chip of the present disclosure, the operator can pre-load different substances in different reaction chambers, for example, during chip production. Thus, the present disclosure enables various forms of detection on the same chip (or on chips of the same design), including nucleic acid amplification reactions, biochemical reactions (e.g., enzyme catalyzed reactions), and immune reactions. In another aspect, the present disclosure enables the detection of different substance in the same reaction or reactions, such that multiple applications on the same chip platform can be performed. For example, to detect a particular nucleic acid fragment in the sample by a nucleic acid amplification reaction on the chip (such as a mutant gene or genes of pathogenic microorganisms), the primer(s) and auxiliary components necessary for specific biochemical reactions with different nucleic acid fragments in the test sample can be pre-loaded in different reaction chambers. In another example, to detect a specific substance or component in the sample by biochemical reaction on the chip (such as glucose or triglycerides), reagents necessary for specific biochemical reactions with the target substance or component in the test sample can be pre-loaded in different reaction chambers. In yet another example, to detect a specific component in the sample by immune reaction on the chip (such as a specific antigen or antibody), reagents necessary for specific immune reactions with the target substance or component can be pre-loaded in the test sample in different reaction chambers.

In any of the preceding embodiments, the microfluidic chip can be used for real-time detection during the reaction or detected after the reaction, for example, by fluorescence, turbidity, color, detection equipment, or direct observation by the naked eyes.

Throughout this disclosure, like reference numerals are used to denote like parts. The present disclosure is further described in conjunction with the drawings. However, the present disclosure is not to be limited to the following examples.

Figure 2:
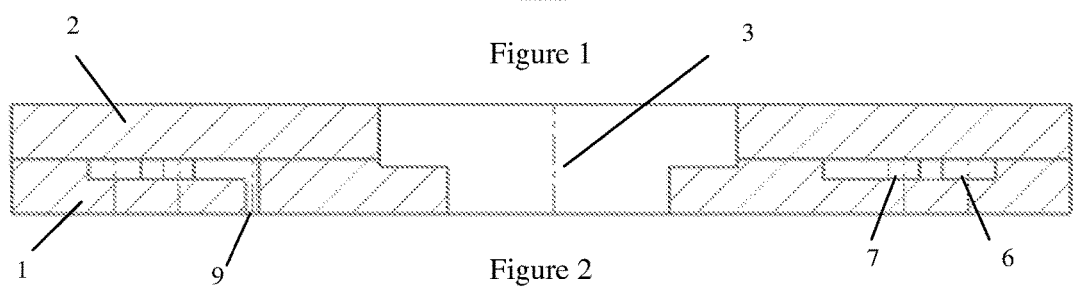
FIG. 2 is a cross section view of a microfluidic chip according to one aspect of the present disclosure.

FIG. 1 is an aerial view of a multi-index detection microfluidic chip (96 holes) according to one aspect of the present disclosure. FIG. 2 is a cross section view of a microfluidic chip according to one aspect of the present disclosure. The microfluidic chip of the present disclosure comprises a bottom plate 1 and a cover plate 2 that matches the bottom plate 1 and seals it. Components of the bottom plate and/or the cover plate can be bonded firmly by using a double faced adhesive tape, which has the desired adhesive strength and resistance to conventional heating temperatures, and which has no significant adverse effects on the specificity of the reactions in the chip. In the center of the microfluidic chip, a through-hole 3 is provided, and the inner edge of the through-hole 3 is provided with a locating notch 8. The through-hole 3 and the locating notch 8 play the role of fixing the chip during centrifugation. In one aspect, because the through-hole 3 and the locating notch 8 fix the chip and at the same time are used as a reference position to earmark the reaction chambers on the chip, only one centrifuge is required to complete the process of uniformly distributing the sample into the reaction chambers. There is provided a wave-shaped main channel 4 on the bottom plate 1, and one end of main channel 4 connects with a sample injection hole 9, while the other end of main channel 4 connects with an exhaust hole 10. The shape of the sample injection hole can be designed to match the standard and conventional plastic tip head used in the biological assays. For example, when the required volume of the sample is between about 20 and about 200 microliters, the diameter of the sample injection hole 9 can be between about 0.75 mm and about 0.9 mm. In some embodiments, the diameter of the sample injection hole 9 is between about 0.75 mm and about 0.80 mm, between about 0.80 mm and about 0.85 mm, or between about 0.85 mm and about 0.90 mm.

As shown in FIG. 1, the wave-shaped main channel 4 connects with a reaction chamber 6 by linking channel 5. In one aspect, the reaction chamber 6 is positioned distal to the through-hole 3, and the junction between linking channel 5 and reaction chamber 6 locates in a line that connects the center of the microfluidic chip and reaction chamber 6. As such, the sample (for example, a liquid sample) loaded into main channel 4 can be distributed into reaction chamber 6 through linking channel 5 by a centrifugal force when the chip rotates.

In one embodiment, as shown in FIG. 1, wave-shaped main channel 4 forms two circles on bottom plate 1. In this example, there is a buffering chamber 7 in each of the linking channels 5. Therefore, the buffering chamber connects each of the valleys of the main channel with its corresponding reaction chamber, and serves as a buffer reservoir for the sample when the sample is distributed from the main channel into the reaction chambers when the chip is subjected to centrifugation. Compared with chips without the buffering chambers, the buffering chamber 7 in the linking channel 5 as shown in FIG. 1 serves three main functions, among others.

First, the buffering chambers ensure that the reaction chambers of the microfluidic chip are filled with the sample after the sample in loaded into the main channel and subjected to centrifugation.

Figure 3:
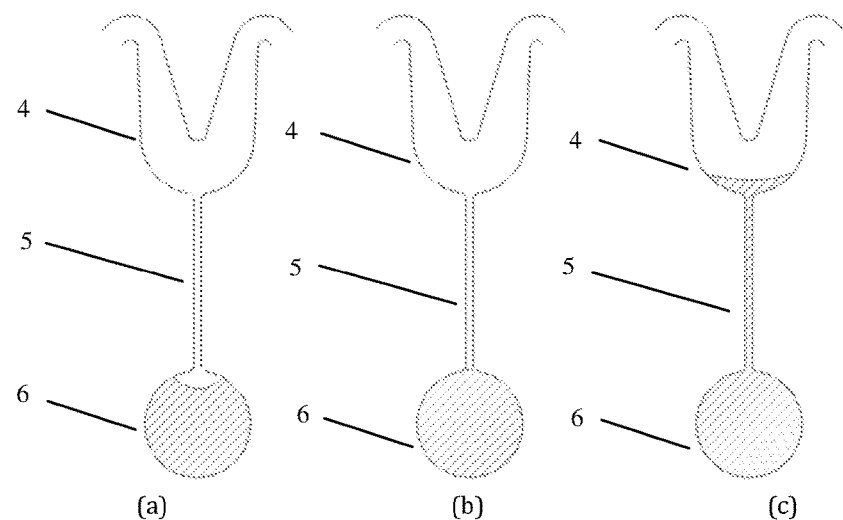
FIGS. 3(a)-(c) show patterns of fluid distribution during centrifugation in a microfluidic chip without buffering chambers. Without buffering chambers, some of the reaction chambers are not fully filled with the sample as shown in FIG. 3(a), some reaction chambers are fully filled with sample as shown in FIG. 3(b) (the ideal situation), while others are overfilled with the sample, which spills out into the linking channel, as shown in FIG. 3(c).

As an example shown in FIG. 3, when there is no buffering chamber 7 and the volume of each reaction chamber 6 is the same as the V-shaped portion of the main channel, some of the reaction chambers may not be fully filled with the sample after centrifugation. This is because when the sample is loaded into the main channel and is distributed in the V-shaped portions of the channel, each V-shaped portion may not have the same amount of the sample. Thus, after centrifugation, the amount of sample collected in the reaction chambers may not be uniform for all the reaction chambers. Some of the reaction chambers are not fully filled with the sample as shown in FIG. 3($a$), others are fully filled with the sample as shown in FIG. 3($b$), and still others are overfilled with the sample, which overflows into the linking channel and/or into the V-shaped portion of the main channel as shown in FIG. 3($c$). Therefore, the inconsistent distribution of sample amount in the reaction chambers will affect reaction results in the reaction chambers, and will directly influence the accuracy of the test results. In another aspect, the residual sample in the V-shaped portion of the main channel (as shown for example in FIG. 3($c$)) may cause the reaction product in the reaction chamber to diffuse to adjacent reaction chambers, causing cross-contamination.

Figure 4:
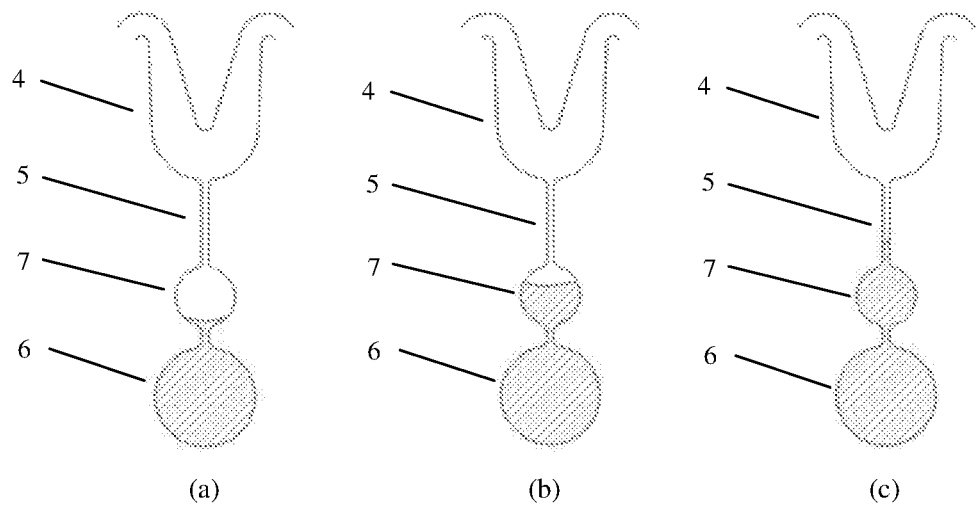
FIGS. 4(a)-(c) show patterns of fluid distribution during centrifugation in a microfluidic chip with buffering chambers. All of the reaction chambers in FIG. 4 are fully filled with the sample (thereby ensuring even distribution of the sample in the reaction chambers), although the sample may reach different levels in the buffering chambers and/or linking channels as shown in FIGS. 4(a)-(c).

In one aspect, the sample in the V-shaped portions of the main channel is distributed to the reaction chambers, and fills about ⅔ of the volume of the buffering chamber after centrifugation. In this case, the uneven distribution of the sample after centrifugation is only reflected in the amount of the sample in the buffering chamber, and this ensures that the reaction chambers are uniformly fully filled with the same amount of the sample, as shown in FIGS. 4($a$)-($c$).

Second, the buffering chamber ensures that the reaction chambers are fully filled with the sample (or reaction mix) even when the reaction chambers are heated during the reaction.

As an example, when there is no buffering chamber 7, even when the sample or reaction mix is uniformly distributed in the reaction chambers after centrifugation, the sample or reaction mix may need to be heated to a certain temperature in order for the reactions to happen. Evaporation of the liquid during heating can result in reduced liquid volume in the reaction chambers and changes in the reagent concentrations. Those changes in reagent concentrations typically are not uniform for all the reaction chambers. The changes in reagent concentrations and the reductions of liquid volume in the reaction chambers will affect the accuracy of the test results.

As such, the buffering chamber in one aspect is directly connected to the linking channel, and the liquid in the buffering chamber will compensate for the loss of liquid volume in the reaction chambers, thereby maintaining that the reaction chambers are fully filled throughout the reaction.

Third, the buffering chambers in one aspect prevent the reaction product in each reaction chamber from diffusing to adjacent reaction chambers and causing cross-contamination.

Typically, when the sample is distributed to the reaction chambers through centrifugation, a liquid film of the sample remains on the inner surface of the linking channel. If two adjacent reaction chambers are connected by a linking channel and are separated only by the linking channel, then the reaction product of each reaction chamber is likely to diffuse into the adjacent chamber through the liquid film and lead to cross-contamination.

In one aspect, the present disclosure designs a buffering chamber in the linking channel to avoid the cross-contamination. Typically, the reagents, target molecules, and reaction products diffuse from higher concentration to lower concentration. For example, when the reaction products (e.g., amplified products from a nucleic acid amplification reaction) diffuse from the reaction chambers, they will diffuse into the buffering chamber first, which reduces the concentration of the diffused products dramatically. As such, the reaction products in the buffering chambers are less likely to further diffuse out into the linking channels, into the main channel, and/or into adjacent reaction chambers. Accordingly, the present disclosure reduces the chance of diffused products to spread to the linking channel and therefore improves the accuracy of test results.

Figure 5:
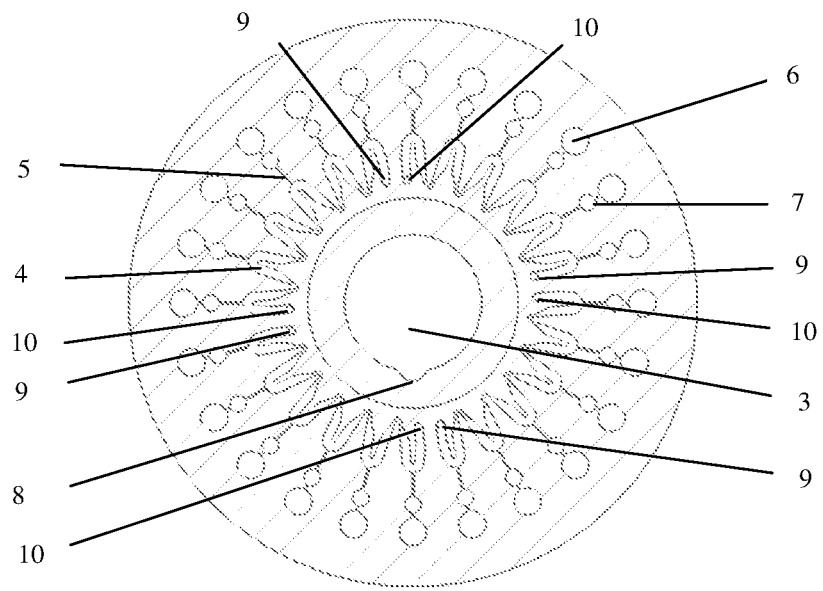
FIG. 5 is an aerial view of a microfluidic chip for multi-index detection, according to one aspect of the present disclosure. 1—Bottom plate; 2—Cover plate; 3—Through-hole; 4—Main channel; 5—Linking channel; 6—Reaction chamber; 7—Buffering chamber; 8—Earmark notch; 9—Sample inlet port; and 10—Exhaust port.

FIG. 5 is an aerial view of a microfluidic chip for multi-index detection, according to one aspect of the present disclosure. In this example, there are four wave-shaped main channels 4 in the bottom plate, and these four main channels form a circle. Furthermore, the end of each main channel 4 connects with the sample injection hole 9, and the other end connects with the exhaust hole 10. Therefore, the reactions chambers on this chip can be grouped into four groups, and members of each group are connected to the same main channel. In this example, the reaction chamber 6 that connects with each main channel 4 can each be pre-loaded with a different substance. In one aspect, the different substances can be detected using the same form of assay, for example, nucleic acid amplification reactions. In another aspect, the different substances can participate in a reaction to detect one or more targets using the same form of assay, for example, nucleic acid amplification reactions. In certain embodiments, the reaction chambers can be pre-loaded with primers and auxiliary components that produce specific biochemical reactions with different nucleic acid fragments of the test sample. Through centrifuging the samples and nucleic acid amplification reactions of the multiple samples, the chip can be used to detect one or more nucleic acid fragments in multiple test samples using the same reaction format (for example, the same PCR cycles) on the same chip. In one aspect, the present disclosure enables simultaneous detection of multiple targets in the same sample. For example, the same sample can be divided into four aliquots and each aliquot is loaded into one of the four main channels in FIG. 5, and each group of reaction chambers contain reagent(s) for detecting a different target molecule in the sample. In one aspect, the present disclosure enables simultaneous detection of the same target(s) in different samples. For example, each one of four different samples can be loaded into one of the four main channels in FIG. 5, and the four groups of reaction chambers contain the same reagent(s) for detecting the same target(s). In one aspect, the present disclosure enables simultaneous detection of different parameters of the same target(s) in a sample. For example, the same sample can be divided into four aliquots and each aliquot is loaded into one of the four main channels in FIG. 5, and each group of reaction chambers contain reagent(s) for detecting a different parameter of the same target(s) in the sample.

Figure 6:
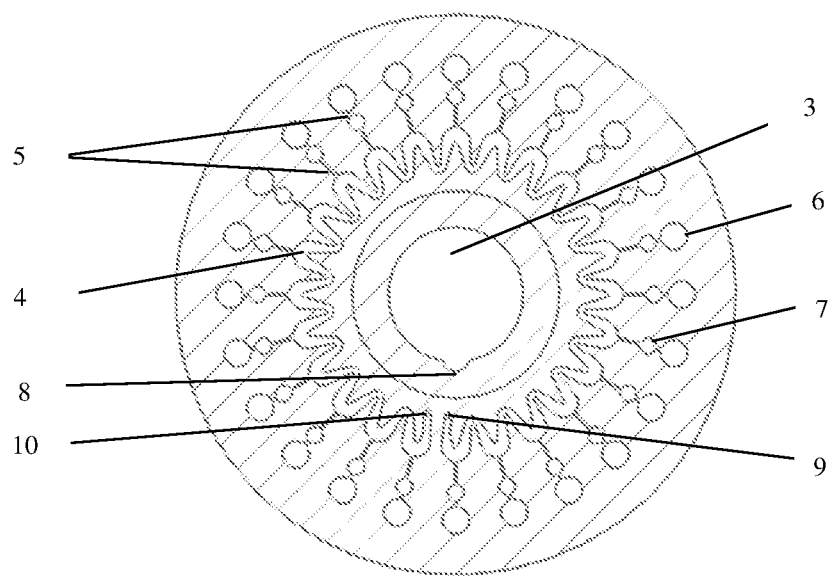
FIG. 6 is an aerial view of a microfluidic chip for multi-index detection, according to one aspect of the present disclosure. 1—Bottom plate; 2—Cover plate; 3—Through-hole; 4—Main channel; 5—Linking channel; 6—Reaction chamber; 7—Buffering chamber; 8—Earmark notch; 9—Sample inlet port; and 10—Exhaust port.

FIG. 6 is an aerial view of a microfluidic chip for multi-index detection, according to another aspect of the present disclosure. In this example, the wave-shape main channel 4 forms a circle. In one aspect, the cross-sectional area at the peak is smaller than the cross-sectional area at the valley in the main channel 4. The ratio of the cross-sectional area at the peak to the cross-sectional area at the valley can be varied, and the ratios can be chosen to facilitate uniform distribution of the samples and to avoid cross-contamination. In some embodiments, the preferred ratio of the narrowest and the widest cross sectional area in the V-shaped portion of the main channel is from about 0.2 to about 1. In particular embodiments, as verified experimentally in FIG. 7 and FIG. 8, if the ratio is less than about 0.2, due to the large resistance in the series of the V-shaped portions of the main channel, it is difficult to add sample into the main channel and subsequently distribute the sample into the reaction chambers. In another aspect, because the cross sectional area of the valley is wider than that of the peak, it is easy to generate bubbles and result in nonuniform distribution of the sample. In addition, if the ratio of the cross-sectional area at the peak to the cross-sectional area at the valley is larger than 1, it will likely lead to nonuniform distribution of the sample to each reaction chamber through centrifugation. Results of experimental validation are described below.

Figure 7:
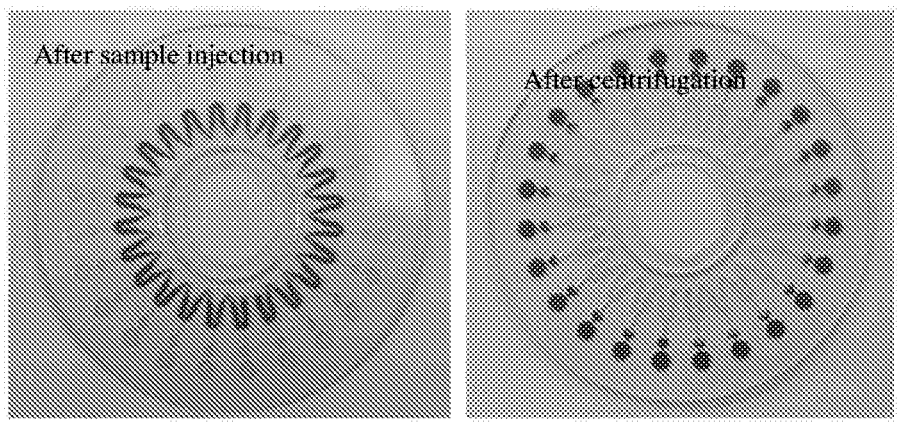
FIG. 7 shows the distribution of a dyed sample after sample injection (left panel) and after centrifugation (right panel). In this figure, the ratio between the narrowest and the widest cross sectional areas in the main channel is 0.3:1.

FIG. 7 shows the distribution of a dyed sample after sample injection (left panel) and after centrifugation (right panel). In this figure, the ratio between the narrowest and the widest cross sectional areas in the main channel is 0.3:1.

Figure 8:
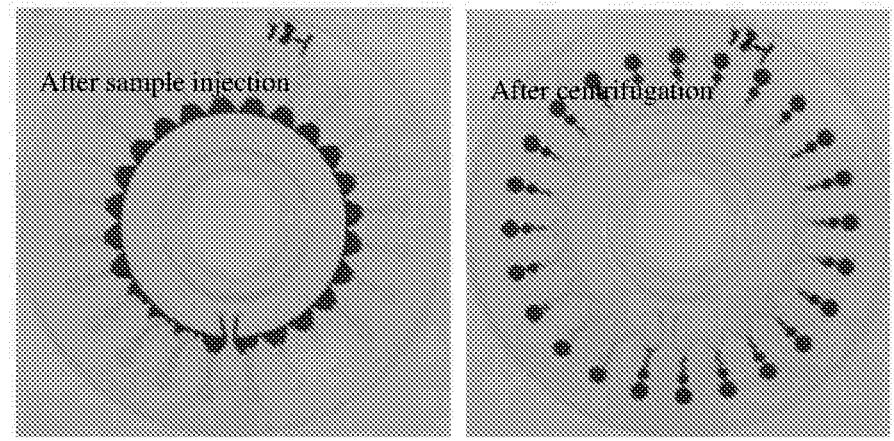
FIG. 8 shows the distribution of a dyed sample after sample injection (left panel) and after centrifugation (right panel). In this figure, the ratio between the narrowest and the widest cross sectional areas in the main channel is less than 0.2:1.

FIG. 8 shows the distribution of a dyed sample after sample injection (left panel) and after centrifugation (right panel). In this figure, the ratio between the narrowest and the widest cross sectional areas in the main channel is less than 0.2:1.

In FIG. 7, there are no bubbles in the injection process, and the sample is uniformly distributed in all reaction chambers after centrifugation. In contrast, in FIG. 8, bubbles are generated in some V-shaped portions of the main channel, and it can be clearly observed that the sample is not uniformly distributed in the reaction chambers after centrifugation.

CN 102369443 A discloses a centrifugal infusion chip, i.e., liquid on the central storage unit of the chip is transported eccentrically to the holes around the central storage unit for adding the sample. The design of the main channel in CN 102369443 A is that the peaks and valleys have the same width, and this design fails to resolve liquid uniformity issues. In other words, the amount of sample added to each sample hole is not equal. In addition, the design that peaks are wider than valleys will generate bubbles in the main channel during the process of adding the sample. Furthermore, CN 102369443 A adds a waste chamber to load excess solutions. Although this design can achieve the consistency of the amount of sample distributed into each of the sample holes, it cannot guarantee that the sample consistently fills the sample holes during the reaction. In addition, this design requires surface modification on the internal surfaces of the microfluidic channel, i.e., hydrophilic treatment of the inner surface of the branch flow channel connected with the sample adding hole, and hydrophobic treatment in the inner surface of the branch flow channel connected with the waste chamber that collects the remaining solutions. All of the steps increase the complexity of the manufacturing process and the difficulty of processing, and increase processing costs.

Figure 9:
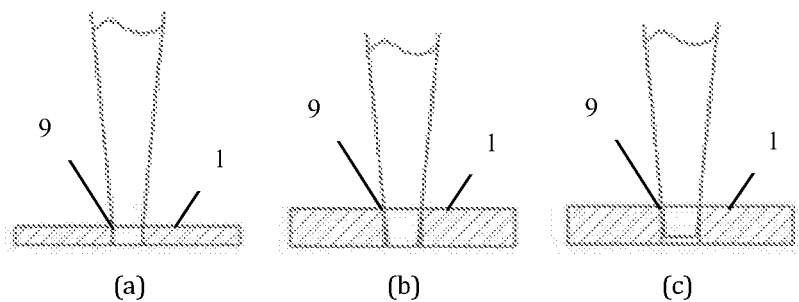
FIGS. 9(a)-(c) are schematics showing loading of the samples into the sample inlet ports of the microfluidic chip.

In certain embodiments, the sample inlet port is set at the bottom plate 1 with a thickness range of between about 0.05 mm and about 1 mm. In some embodiments, the diameter of the sample inlet port is between about 0.75 mm and about 0.9 mm, and a standard 200-microliter tip head in biological experiment can be used to add the sample into the sample inlet port, without the sample escaping from the channel when loading. As shown in FIG. 9, the diameter of micropipettor tip is 0.75 mm, and the diameter of the cross section that is 1 mm from the tip is 0.9 mm. Therefore, in this example, if the diameter of the sample inlet hole is smaller than 0.75 mm, it is impossible to insert the micropipettor tip into the sample inlet hole. In another aspect, if the diameter of the sample inlet hole is larger than 0.9 mm, there is a gap between the tip and side wall of the sample inlet hole, which will lead to sample leakage during the process of sample injection. Therefore, in some embodiments, the optimal range of the size of the sample inlet port is between about 0.75 mm and about 0.9 mm. If the diameter of the sample inlet hole is 0.75 mm, the micropipettor tip cannot be inserted into the sample inlet hole as shown in FIG. 9(a), resulting in sample leakage. If the diameter of the sample inlet hole is 0.9 mm, the tip head needs to be inserted fully into the sample inlet port, thereby causing the tip to touch the bottom of the chip and block loading of the sample. This can easily clog the channel and cause difficulties in adding samples, as shown in FIG. 9(b). In one aspect, the diameter of the sample inlet port is about 0.8 mm. In this case, there is a gap between the tip end and the bottom of the chip after inserting the tip head, as shown in FIG. 9(c), thereby allowing accurate loading of the sample without obstruction. Under these circumstances, samples can be added from a pipettor to the main channel 4 of the chip conveniently, accurately, and without leakage.

The microfluidic chip can comprise any suitable material. In one example, the microfluidic chip comprise a material selected from the group consisting of a silicon, a plastic, a glass, a ceramic, a rubber, a metal, a polymer, a paper and a combination thereof. In one aspect, the microfluidic chip is injection molded. In another aspect, the plastic is selected from the group consisting of polycarbonate, methyl methacrylate, polystyrene, acrylonitrile-butadiene-styrene (ABS), polyethylene and polypropylene. In still another example, the microfluidic chip comprises a glass. In one aspect, the microfluidic chip is fabricated by a method selected from the group consisting of gluing, dicing/cutting, slicing, anodic bonding, ultrasonic welding, and a combination thereof.

In one aspect, the present disclosure is directed to an article of manufacture, which article of manufacture comprises: a) a packaging material; b) a microfluidic chip disclosed herein; optionally, c) a label indicating that the article is for an assay, for example, for assaying an analyte; and optionally, d) an instruction, for example, for using the article of manufacture for an assay.

The disclosure comprises kits comprising a microfluidic chip or an assay device disclosed herein. For example, kits for diagnosing or aiding in the diagnosis of a condition or a disease (e.g., cancer) or for monitoring a condition or a disease are included. In one embodiment, the kit comprises one or more reagents for detecting one or more analytes, for example, biomarkers associated with a condition or a disease. The reagents comprise labeled compounds or agents capable of detecting a polypeptide or an mRNA encoding a polypeptide corresponding to a biomarker in a biological sample, and means for determining the absence, presence, and/or amount of the polypeptide or mRNA in the sample (e.g., an antibody which binds the polypeptide or an oligonucleotide probe which binds to DNA or mRNA encoding the polypeptide). Suitable reagents for binding with a polypeptide corresponding to a biomarker include antibodies, antibody derivatives, antibody fragments, and the like. Suitable reagents for binding with a nucleic acid (e.g., a genomic DNA, an mRNA, a spliced mRNA, a cDNA, or the like) include complementary nucleic acids. In one embodiment, the kit comprises a reference sample. In one aspect, the reference sample is used to compare the results obtained from the sample being tested. The kit can also comprise other components such as a buffering agent, a preservative, or a protein stabilizing agent. The kit can further comprise components necessary for detecting a detectable label (e.g., an enzyme or a substrate).

Each component of the kit can be enclosed within an individual container and all of the various containers can be within a single package, along with instructions for interpreting the results of the assays performed using the kit.

In one aspect, the article of manufacture or kit disclosed herein is used for diagnosing a condition or a disease in a subject, assessing the risk of a subject developing a condition or a disease, and/or evaluating prognosis of a condition or a disease in a subject, for example, following treatment of the subject with a therapy. In one aspect, the article of manufacture is used to assay a sample obtained from a subject having or suspected of having a condition or a disease.

C. Use of the Microfluidic Chip

The present microfluidic chip can be used in any suitable assay to improve assay precision, reproducibility, and/or sensitivity, particularly for the assays involving small reaction volumes. For instance, the microfluidic chip can be used in assaying the interaction between various moieties, e.g., nucleic acids, immunoreactions involving proteins, interactions between a protein and a nucleic acid, a ligand-receptor interaction, and small molecule and protein or nucleic acid interactions, etc.

The present microfluidic chip can be used to assay any analyte, e.g., a cell, a cellular organelle, a virus, a molecule and an aggregate or complex thereof. Exemplary cells include animal cells, plant cells, fungus cells, bacterium cells, recombinant cells and cultured cells. Animal, plant, fungus, bacterium cells can be derived from any genus or subgenus of the Animalia, Plantae, fungus or bacterium kingdom. Cells derived from any genus or subgenus of ciliates, cellular slime molds, flagellates and microsporidia can also be assayed by the present methods. Cells derived from birds such as chickens, vertebrates such as fish and mammals such as mice, rats, rabbits, cats, dogs, pigs, cows, ox, sheep, goats, horses, monkeys and other non-human primates, and humans can be assayed by the present methods.

For animal cells, cells derived from a particular tissue or organ can be assayed. For example, connective, epithelium, muscle or nerve tissue cells can be assayed. Similarly, cells derived from an internal animal organ such as brain, lung, liver, spleen, bone marrow, thymus, heart, lymph, blood, bone, cartilage, pancreas, kidney, gall bladder, stomach, intestine, testis, ovary, uterus, rectum, nervous system, gland, internal blood vessels, etc. can be assayed. Further, cells derived from any plants, fungi such as yeasts, bacteria such as eubacteria or archaebacteria can be assayed. Recombinant cells derived from any eucaryotic or prokaryotic sources such as animal, plant, fungus or bacterium cells can also be assayed. Body fluid such as blood, urine, saliva, bone marrow, sperm or other ascitic fluids, and subfractions thereof, e.g., serum or plasma, can also be assayed.

Exemplary cellular organelles include nuclei, mitochondria, chloroplasts, ribosomes, ERs, Golgi apparatuses, lysosomes, proteasomes, secretory vesicles, vacuoles and microsomes. Exemplary molecules include inorganic molecules, organic molecules and a complex thereof. Exemplary organic molecules include amino acids, peptides, proteins, nucleosides, nucleotides, oligonucleotides, nucleic acids, vitamins, monosaccharides, oligosaccharides, carbohydrates, lipids and a complex thereof.

Any amino acids can be assayed by the present microfluidic chip. For example, a D- and a L-amino-acid can be assayed. Any proteins or peptides can be assayed by the present microfluidic chip. For example, enzymes, transport proteins such as ion channels and pumps, nutrient or storage proteins, contractile or motile proteins such as actins and myosins, structural proteins, defense protein or regulatory proteins such as antibodies, hormones and growth factors can be assayed. Proteineous or peptidic antigens can also be assayed.

Any nucleosides can be assayed by the present microfluidic chip. Examples of such nucleosides include adenosine, guanosine, cytidine, thymidine and uridine. Any nucleotides can be assayed according to the present disclosure. Examples of such nucleotides include AMP, GMP, CMP, UMP, ADP, GDP, CDP, UDP, ATP, GTP, CTP, UTP, dAMP, dGMP, dCMP, dTMP, dADP, dGDP, dCDP, dTDP, dATP, dGTP, dCTP and dTTP. Any nucleic acids, including single-, double and triple-stranded nucleic acids, can be assayed by the present microfluidic chip. Examples of such nucleic acids include DNA, such as A-, B- or Z-form DNA, and RNA such as mRNA, miRNA, piRNA, tRNA and rRNA.

Any vitamins can be assayed by the present microfluidic chip. For example, water-soluble vitamins such as thiamine, riboflavin, nicotinic acid, pantothenic acid, pyridoxine, biotin, folate, vitamin B 12 and ascorbic acid can be assayed. Similarly, fat-soluble vitamins such as vitamin A, vitamin D, vitamin E, and vitamin K can be assayed.

Any monosaccharides, whether D- or L-monosaccharides and whether aldoses or ketoses, can be assayed the present microfluidic chip. Examples of monosaccharides include triose such as glyceraldehyde, tetroses such as erythrose and threose, pentoses such as ribose, arabinose, xylose, lyxose and ribulose, hexoses such as allose, altrose, glucose, mannose, gulose, idose, galactose, talose and fructose and heptose such as sedoheptulose.

Any lipids can be assayed by the present microfluidic chip. Examples of lipids include triacylglycerols such as tristearin, tripalmitin and triolein, waxes, phosphoglycerides such as phosphatidylethanolamine, phosphatidylcholine, phosphatidylserine, phosphatidylinositol and cardiolipin, sphingolipids such as sphingomyelin, cerebrosides and gangliosides, sterols such as cholesterol and stigmasterol and sterol fatty acid esters. The fatty acids can be saturated fatty acids such as lauric acid, myristic acid, palmitic acid, stearic acid, arachidic acid and lignoceric acid, or can be unsaturated fatty acids such as palmitoleic acid, oleic acid, linoleic acid, linolenic acid and arachidonic acid.

The present microfluidic chip can be used to assay any sample. For example, the present method can be used to assay a mammalian sample. Exemplary mammals include bovines, goats, sheep, equines, rabbits, guinea pigs, murine, humans, felines, monkeys, dogs and porcines. The present microfluidic chip can also be used to assay a clinical sample. Exemplary clinical samples include serum, plasma, whole blood, sputum, cerebral spinal fluid, amniotic fluid, urine, gastrointestinal contents, hair, saliva, sweat, gum scrapings and tissue from biopsies. Preferably, the present microfluidic chip is used to assay a human clinical sample.

Any suitable reagents can be used in an assay according to the present disclosure. In one aspect, the reagents used in the present disclosure bind or interact specifically with an analyte in a sample. Exemplary reagents include cells, cellular organelles, viruses, molecules and an aggregate or complex thereof. In one aspect, the reagent is an antibody, or a nucleic acid.

The present microfluidic chip can be used in any suitable assay format, for example, in a direct assay format, a sandwich assay format or a competition assay format. In one embodiment, a different plurality of reagents are used to assay a single analyte. In another embodiment, a different plurality of reagents are used to assay a different plurality of analytes. In still another embodiment, a plurality of reagents are attached to the inner surface of the reaction chamber, and is used, for example, to assay one or more analytes in one or more samples.

The present microfluidic chip can be used to detect any interaction(s) among moieties selected from the group consisting of a cell, a cellular organelle, a virus, a molecule and an aggregate or complex thereof. For example, interactions between or among macromolecules, such as DNA-DNA, DNA-RNA, RNA-RNA, DNA-protein, RNA-protein and protein-protein, etc., interactions can be analyzed. In other embodiments, macromolecule-small molecule or small molecule-small molecule interactions are detected or analyze using the present microfluidic chip. More complex interactions including interactions among more than two moieties can also be detected and/or analyzed according to the present disclosure. When DNA-DNA, DNA-RNA, RNA-RNA interactions are to be detected, the contacting, i.e., hybridizing, step, can be conducted under suitable condition, e.g., under low, middle or high stringency, after samples or reagents are delivered to the reaction volumes according to the present disclosure.

The interaction between a test moiety and a plurality of target moieties can be detected by any suitable methods, and the present microfluidic chip can be made to suit the particular detection method. For example, the test moiety and/or target moieties can be labeled to facilitate detection. Any suitable label can be used. Exemplary labels include a radioactive, a fluorescent, a chemical, an enzymatic, a luminescent and a FRET (fluorescence resonance energy transfer) label. The luminescent label can be a chemiluminescent label or a bioluminescent label. The labels can be attached or conjugated, directly or indirectly, to the test moiety alone, the target moiety alone, or on both. The read-out can be a positive or a negative signal. Any suitable assay formats, including sandwich or competitive formats, can be used. Any of the samples or reagents, including the labels, primers or dNTPs of a PCR reaction, or an enzyme, can be delivered using the present microfluidic chip.

In one embodiment, the present microfluidic chip is used to detect interaction between or among a test moiety and a plurality of genes, gene fragments or their encoded products. For instance, the plurality of target genes, gene fragments or their encoded products are involved in a biological pathway, belong to a group of proteins with identical or similar biological function, expressed in a stage of cell cycle, expressed in a cell type, expressed in a tissue type, expressed in an organ type, expressed in a developmental stage, proteins whose expression and/or activity is altered in a disease or disorder type or stage, or proteins whose expression and/or activity is altered by drug or other treatments.

The present microfluidic chip can be used in detecting interaction between or among a single test moiety or substance and a plurality of target moieties. Preferably, the present methods are used in high-throughput mode, e.g., in detecting a plurality of target moieties, and/or interaction between or among a plurality of test moieties or substances. The interaction between a plurality of test moieties or substances and a plurality of target moieties can be detected simultaneously or sequentially.

Microfluidic chips of the present the present disclosure can be used in a variety of applications and reactions, including but not limited to, nucleic acid amplification reactions, biochemical reactions, immune reactions, and so on. The use of the process is illustrated by an example of isothermal amplification reaction as described below.

Isothermal amplification reaction for bacteria genes and bacteria detection can be performed by combining the chip platform of the present disclosure with an isothermal amplification kit and RTisochip™-A isothermal amplification microfluidic chip nucleic acid analyzer. The detection principle is to utilize the isothermal amplification technology, and the reaction can be carried out at a constant temperature (e.g., 65° C.) by using polymerases with a strand displacement function. Samples of positive amplification will produce a similar real-time fluorescence constant S-shaped amplification curve by using SYBR Green to detect fluorescence in real time, so that it completes the amplification and the detection of target genes through one step. In one aspect, a characteristic of the present disclosure is to combine the method of isothermal amplification and microfluidic chip technology, which can execute high-throughput parallel detection of a variety of nucleic acid target sequences at the same time.

In one embodiment, there are twenty-four reaction chambers in each chip, each reaction chamber embedding and/or containing a set of primers that is used for amplification and detection of a particular kind of nucleic acid target sequence. Two of twenty-four reaction chambers are embedded with reference substances as negative and positive control samples, and the rest of twenty-four reaction chamber are embedded with reagents for twenty-two different target nucleic acid sequences. Therefore, the chip can be used to detect twenty-two target nucleic acid sequences, for example, each from a particular strain of bacteria.

First, the test sample DNA is mixed with amplification reagents and then injected into the chip. The sample can be from sputum, oral swab, or blood of a patient or an individual suspected of having a disease or a condition such as bacterial infection. In other examples, the sample can comprise blood, effusion, urine, bone marrow sample, ascitic fluid, pelvic wash fluid, pleural fluid, spinal fluid, lymph, serum, mucus, sputum, saliva, semen, ocular fluid, extract of nasal, throat or genital swab, cell suspension from digested tissue, extract of fecal material, and/or cultured cells of either mixed types and/or mixed sizes. Nucleic acid such as DNA or RNA can be extracted from the samples, for example, using the Crystal Core® universal bacterial DNA rapid extraction kit from CapitalBio Corporation.

If there are residual solutions at the sample inlet port and/or the exhaust port, the residual solutions can be wiped off with an absorbent paper. A sealing membrane can then be used to cover the sample inlet port and/or the exhaust port.

The chip is then placed into the RTisochip™-A isothermal amplification microfluidic chip nucleic acid analyzer after loading the sample, for the amplification reaction to be completed. Each reaction chamber in the chip undergoes independent isothermal amplification reaction at the same time, and real-time fluorescence detection is accomplished by an isothermal amplification instrument. If an S-shaped amplification curveis detected in a reaction chamber, then the detection index corresponding to the reaction chamber is positive.

Thus, the present microfluidic chips and methods can be used to detect a number of infectious diseases or infection states in a subject. Pathogenic viruses include, but are not limited to, Retroviridae (e.g., human immunodeficiency viruses, such as HIV-1 (also referred to as HTLV-III, LAV or HTLV-III/LAV, or HIV-III); and other isolates, such as HIV-LP; Picornaviridae (e.g., polio viruses, hepatitis A virus; enteroviruses, human coxsackie viruses, rhinoviruses, echoviruses); Calciviridae (e.g., strains that cause gastroenteritis); Togaviridae (e.g., equine encephalitis viruses, rubella viruses); Flaviridae (e.g., dengue viruses, encephalitis viruses, yellow fever viruses); Coronaviridae (e.g., coronaviruses); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g., influenza viruses); Bungaviridae (e.g., Hantaan viruses, bunga viruses, phleboviruses and Nairo viruses); Arena viridae (hemorrhagic fever viruses); Reoviridae (e.g., reoviruses, orbiviurses and rotaviruses); Bimaviridae; Hepadnaviridae (Hepatitis B virus); Parvoviridae (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes viruses); Poxyiridae (variola viruses, vaccinia viruses, pox viruses); and Iridoviridae (e.g., African swine fever virus); Hepatitis C virus; and unclassified viruses (e.g., the agent of delta hepatitis (thought to be a defective satellite of hepatitis B virus); Norwalk and related viruses, and astroviruses).

Pathogenic bacteria include, but are not limited to, *Helicobacterpyloris, Borelia burgdorferi, Legionella pneumophila, Mycobacteria* sps (e.g. *M. tuberculosis, M. avium, M. intracellulare, M. kansaii, M. gordonae*), *Staphylococcus aureus, Neisseria gonorrhoeae, Neisseria meningitidis, Listeria monocytogenes, Streptococcus pyrogenes* (Group A *Streptococcus*), *Streptococcus agalactiae* (Group B *Streptococcus*), *Streptococcus* (*viridans* group), *Streptococcus faecalis, Streptococcus bovis, Streptococcus* (anaerobic sps.), *Streptococcus pneumoniae*, pathogenic *Campylobacter* sp., *Enterococcus* sp., *Haemophilus influenzae, Bacillus anthracis, Corynebacterium diphtheriae, Corynebacterium* sp., *Erysipelothrix rhusiopathiae, Clostridium perfringens, Clostridium tetani, Enterobacter aerogenes, Klebsiella pneumoniae, Pasturella multocida, Bacteroides* sp., *Fusobacterium nucleatum*, pathogenic strains of *Escherichia coli, Streptobacillus moniliformis, Treponema pallidium, Treponema pertenue, Leptospira*, and *Actinomyces israelli*.

Infectious fungi include, but are not limited to, *Cryptococcus neoformans, Histoplasma capsulatum, Coccidioides immitis, Blastomyces dermatitidis, Chlamydia trachomatis, Candida albicans*.

Infectious protozoa include, but are not limited to, *Plasmodium* spp., e.g., *Plasmodium falciparum*; Trypanosomes, e.g., *Trypanosoma cruzi*; and *Toxoplasma gondii*.

It is to be understood that the present microfluidic chips are suitable for detection of the above infectious agents by detecting their genetic material, for example, by PCR of specific nucleic acid sequences that are indicative of the infectious agents, by detecting proteins, lipids, or polysaccharides that are indicative of the infectious agents, and/or by detecting host responses to the infectious agents (e.g., host antibodies to the infectious agents).

Allergens include, but are not limited to, pollens, insect venoms, animal dander dust, fungal spores and drugs (e.g. penicillin). Examples of natural, animal and plant allergens include proteins specific to the following genera: Canine (*Canis familiaris*); *Dermatophagoides* (e.g. *Dermatophagoides farinae*); *Felis* (*Felis domesticus*); *Ambrosia* (*Ambrosia artemiisfolia*; *Lolium* (e.g. *Lolium perenne* or *Lolium multiflorum*); *Cryptomeria* (*Cryptomeria japonica*); *Alternaria* (*Alternaria alternata*); *Alder*; *Alnus* (*Alnus gultinosa*); *Betula* (*Betula verrucosa*); *Quercus* (*Quercus alba*); *Olea* (*Olea europa*); *Artemisia* (*Artemisia vulgaris*); *Plantago* (e.g. *Plantago lanceolata*); *Parietaria* (e.g. *Parietaria officinalis* or *Parietaria judaica*); *Blattella* (e.g. *Blattella germanica*); *Apis* (e.g. *Apis multiflorum*); *Cupressus* (e.g. *Cupressus sempervirens, Cupressus arizonica* and *Cupressus macrocarpa*); *Juniperus* (e.g. *Juniperus sabinoides, Juniperus virginiana, Juniperus communis* and *Juniperus ashei*); *Thuya* (e.g. *Thuya orientalis*); *Chamaecyparis* (e.g. *Charnaecyparis obtusa*); *Periplaneta* (e.g. *Periplaneta americana*); *Agropyron* (e.g. *Agropyron repens*); *Secale* (e.g. *Secale cereale*); *Triticum* (e.g. *Triticum aestivum*); *Dactylis* (e.g. *Dactylis glomerata*); *Festuca* (e.g. *Festuca elatior*); *Poa* (e.g. *Poa pratensis* or *Poa compressa*); *Avena* (e.g. *Avena sativa*); *Holcus* (e.g. *Holcus lanatus*); *Anthoxanthum* (e.g. *Anthoxanthum odoratum*); *Arrhenatherum* (e.g. *Arrhenatherum elatius*); *Agrostis* (e.g. *Agrostis alba*); *Phleum* (e.g. *Phleum pratense*); *Phalaris* (e.g. *Phalaris arundinacea*); *Paspalum* (e.g. *Paspalum notatum*); *Sorghum* (e.g. *Sorghum halepensis*); and *Bromus* (e.g. *Bromus inermis*). Use of epitopes from the above allergens in the present methods for antibody detection and analysis is also envisaged. Using this method, host responses to the allergens such as antibodies generated in the host's bodily fluid can be assayed. The presently disclosed microfluidic chips are particularly suitable for highly sensitive, multiplexed detection of the host antibodies.

The following embodiments are intended to further describe and illustrate various aspects of the present disclosure, but not to limit, the scope of the present disclosure in any manner, shape, or form, either explicitly or implicitly.

Embodiment 1

A multi-index detection microfluidic chip, characterized in that: the microfluidic chip includes a bottom plate and a cover plate that matches the bottom plate and seals it; the center of this microfluidic chip has a through-hole; the bottom plate has one or more wave-shaped main channel, one end of each of the main channel connects to the sample injection hole on the bottom plate, the other end connects to the exhaust hole on the bottom plate; the valley on the main channel is far from direction of the through-hole, and peak is near from direction of the through-hole; any valley on the main channel connects to a reaction chamber by the linking channels; and the linking channels have buffering chambers.

Embodiment 2

A microfluidic chip according to Embodiment 1, characterized in that the volume of the buffering chamber is about 0.2~ about 0.8 times of that of the reaction chamber.

Embodiment 3

A microfluidic chip according to Embodiment 1 or 2, characterized in that the junctions between the linking channels and the reaction chambers locate in a connecting line of the center of the microfluidic chip and the reaction chamber.

Embodiment 4

A microfluidic chip according to any one of Embodiments 1-3, characterized in that in the bottom plate, the main channels are distributed in a circle.

Embodiment 5

A microfluidic chip according to any one of Embodiments 1-4, characterized in that in the bottom plate, one or more main channels form one or more circles.

Embodiment 6

A microfluidic chip according to any one of Embodiments 1-5, characterized in that the volume of reaction chamber is about 0.1~ about 5 µL; and that the volume of any V-shaped portion of the main channel is about 1.2~ about 1.8 times of the reaction chamber which is connected with the V-shaped portion.

Embodiment 7

A microfluidic chip according to any one of Embodiments 1-6, characterized in that the cross sectional ratio between the narrowest and the widest area in the main channel is about 0.2~about 1; and when this ratio is less than about 1, the cross section of the peak is smaller than that of the valley.

Embodiment 8

A microfluidic chip according to any one of Embodiments 1-7, characterized in that the microfluidic chip contains about 5~ about 100 reaction chambers.

Embodiment 9

A microfluidic chip according to any one of Embodiments 1-8, characterized in that the thickness of the bottom plate and that of the cover plate are about 0.05~about 5 mm; and the depth of the main channel, the depth of the reaction chamber, the depth of the linking channel, and the depth of the buffering chamber are about 40 µm~ about 4 mm.

Embodiment 10

A microfluidic chip according to any one of Embodiments 1-9, characterized in that the sample injection holes of the bottom plate are round, and the size of the sample injection hole is matched with a standard tip head; and the inner edge of through-hole is provided with a locating notch.

EXAMPLE 1

Microfluidic Chip for Multiplex Gene Amplification and Rapid Detection of Pathogens In this example, a mini disc-like microfluidic chip (PathoDisc) was developed to carry out parallel isothermal amplification of multiplex interest target genes in one sample. A disc operating instrument equipped with smart temperature control module and fluorescence signal detection system was constructed to measure the results. In one aspect, by combining a fast nucleic acid extraction kit and appropriate isothermal amplification reagents, the chip was able to detect 13 types of pathogens in parallel in clinical samples such as sputum or bronchoalveolar lavage fluids in less than 2 hours. The microfluidic chip was able to perform parallel detection of multiple targets in one assay run and its application in the diagnosis of infectious diseases (e.g., severe pneumonia) was demonstrated.

Chip design and fabrication. The chip has one main fluid channel for sample loading, and 24 reaction wells for nucleic acid amplification. The main channel has 24 "V-shapes" each corresponding to one reaction well. The chip was fabricated with injection molding. Then the specific probe was loaded onto the reaction well. After that the chip was enclosed with a cover.

Figure 10:
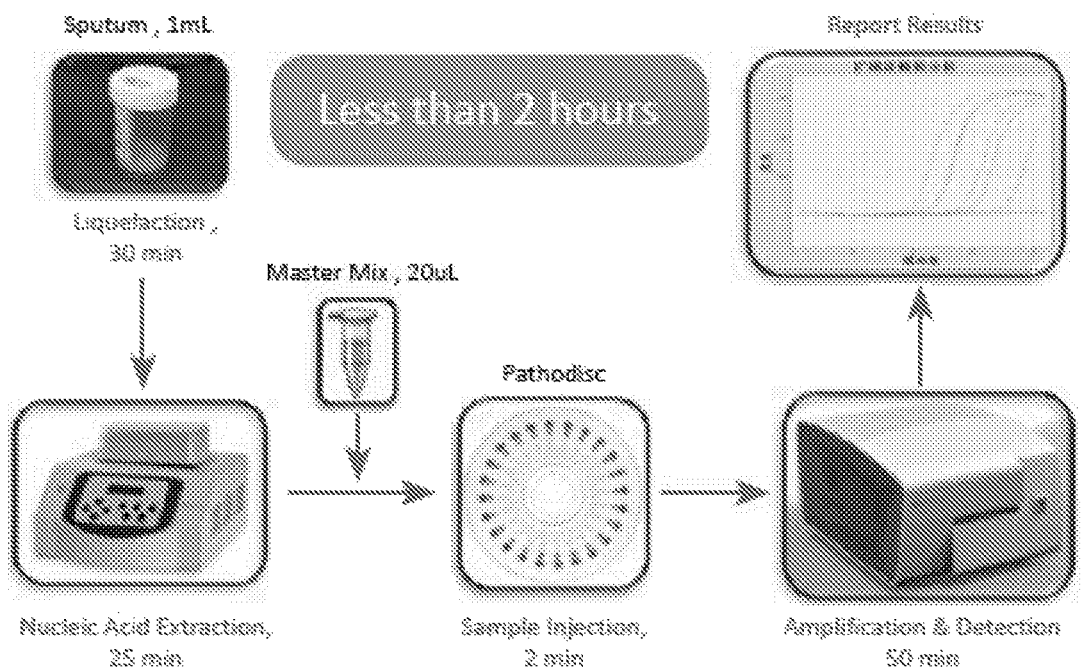
FIG. 10 is a schematic of experimental procedures for using a microfluidic chip to detect pathogens, according to one aspect of the present disclosure.

Experimental setup. In one aspect, the total experiment time was no more than 2 hours from getting the sputum or bronchoalveolar lavage fluids samples to reporting the detection results. The experiment procedure is shown in FIG. 10.

Figure 11:
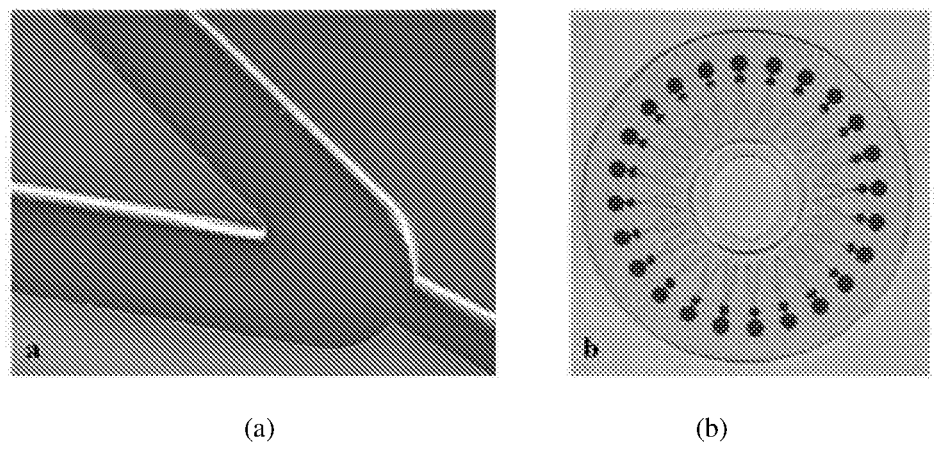
FIG. 11(a) is an SEM image of a microfluidic channel, according to one aspect of the present disclosure.
FIG. 11(b) is a photo of a microfluidic chip after sample loading, according to one aspect of the present disclosure.

Verification of the chip design and fabrication. The chip fabrication was verified by SEM and microscope. No cross contamination between the reaction wells and the channel was observed (FIG. 11(a): SEM image of the microfluidic channel). FIG. 11(b) is the photo of the microfluidic chip structure with 24 reaction wells, after loading sample. To achieve a higher quality of the photo, the sample was colored with ink.

Figure 12:
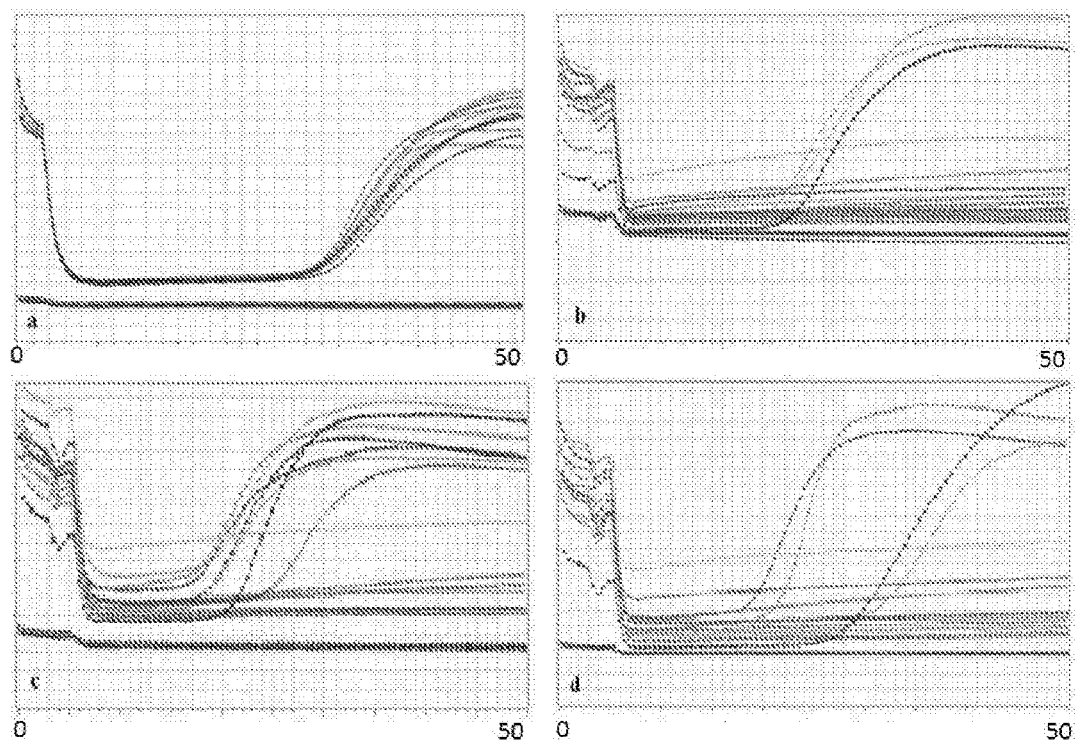
FIGS. 12(a)-(d) are real-time fluorescent amplification curves with the x-axis indicating time (minute) and the y-axis indicating fluorescence intensity (arbitrary unit).

Evaluation of the performance of the chip. The performance of the PathoDisc was tested with reference preparation using real-time fluorescent amplification curves. When a specific probe was matched with the nucleic acid that was detected, the primary curve shape would be like "S", otherwise, a straight line. FIG. 12(a) shows 12 repeat test results with 1000 copies/μL Mtb (*Mycobacterium tuberculosis* complex) preparation, demonstrating the test result was highly repeatable. FIG. 12(b) shows test results of a clinical sample showing that there were Spn bacteria in the sample. Performance of the analysis was not affected even when there were high concentrations of nucleic acids from multiple bacteria species present simultaneously in the sample (FIG. 12(c)). The results also show that the analyzing sensitivity of PathoDisc was not influenced after sample storage at −20° C. for 11 months (FIG. 12(d)).

Clinical samples detection validated by gene sequencing. PathoDisc was used to test 140 clinical samples and the results were verified using gene sequencing. The results are shown in Table 1. Thus, in one aspect, the disc-like microfluidic chip (PathoDisc) is suitable for fast multiplex gene detection in one sample. In other aspects, in conjunction with corresponding instruments and appropriate isothermal amplification reagents, the chip can detect 13 types of bacteria in parallel with the capability of detecting 500 bacteria in 1 mL clinical sample (such as sputum or bronchoalveolar lavage fluids) in less than 2 hours.

TABLE 1

The results of clinical samples.

| | Bacteria species | Abbr. | Clinical Sensitivity | Clinicial Specificity |
|---|---|---|---|---|
| 1 | *Streptococcus pneumoniae* | Spn | 5/6 | 99% |
| 2 | *Staphylococcus aureus* | Sau | 9/9 | 100% |
| 3 | *Escherichia coli* | Eco | 1/1 | 100% |
| 4 | *Klebsiella pneumoniae* | Kpn | 4/4 | 100% |
| 5 | *Pseudomonas aeruginosa* | Pae | 11/11 | 98% |
| 6 | *Acinetobacter baumannii* | Aba | 17/19 | 100% |
| 7 | *Stenotrophomonas maltophilia* | Sma | 9/9 | 100% |
| 8 | *Haemophilus influenzae* | Hin | 2/3 | 100% |
| 9 | *Legionella pneumophila* | Lpn | 2/2 | 100% |
| 10 | *Mycoplasma pneumoniae* | Mpn | 16/16 | 97% |
| 11 | *Chlamydophilia pneumoniae* | Cpn | 0/0 | 100% |
| 12 | methicillin-resistant *Staphylococci* | MRS | 26/26 | 96% |
| 13 | *Mycobacterium tuberculosis* complex | Mtb | 4/6 | 100% |

What is claimed is:

1. A microfluidic chip, comprising:
   (1) a bottom plate comprising:
      at least one wave-shaped main channel comprising at least one valley and at least one peak;
      at least one sample inlet port;
      at least one exhaust port; and
      at least one reaction chamber,
   wherein one end of said at least one wave-shaped main channel is connected to said at least one sample inlet port, and the other end is connected to said at least one exhaust port,
   wherein said at least one valley points away from the center of said bottom plate, and said at least one peak points toward the center of said bottom plate, and
   wherein said at least one valley of said main channel is connected to said at least one reaction chamber; and
   (2) a cover plate fittingly engaging said bottom plate;
   wherein said bottom plate further comprises at least one linking channel, said at least one linking channel connecting said at least one valley of said at least one main channel to said at least one reaction chamber, and wherein said at least one linking channel comprises one or more buffering chambers;
      wherein said at least one main channel forms a plurality of concentric circles on said bottom plate.

2. The microfluidic chip of claim 1, wherein said bottom plate further comprises a central through-hole.

3. The microfluidic chip of claim 2, wherein said bottom plate further comprises an earmark.

4. The microfluidic chip of claim 3, wherein said earmark is a notch located on the inner edge of said central through-hole.

5. The microfluidic chip of claim 2, wherein said cover plate comprises a central through-hole which aligns with said central through-hole of said bottom plate.

6. The microfluidic chip of claim 1, wherein said cover plate matches and seals said bottom plate.

7. The microfluidic chip of claim 1, wherein said bottom plate comprises a plurality of reaction chambers for multi-index detection, wherein said at least one wave-shaped main channel comprises a plurality of peaks and valleys, wherein each of at least about 50% of said plurality of valleys is connected to a respective reaction chamber of said plurality of reaction chambers.

8. The microfluidic chip of claim 7, wherein each of said reaction chambers comprises a reagent for detecting a target in a sample.

9. The microfluidic chip of claim 7, wherein at least one of said reaction chambers comprise at least two reagents, each of which detects a different target.

10. The microfluidic chip of claim 1, wherein the volume of said one or more buffering chamber is between about 0.2 to about 0.8 times of the volume of said at least one reaction chamber.

11. The microfluidic chip of claim 1, wherein the junction between said at least one linking channel and said at least one reaction chamber is located on the line between the center of said bottom plate and the center of said reaction chamber.

12. The microfluidic chip of claim 1, wherein the volume of said at least one reaction chamber is between about 0.1 µL and about 5 µL.

13. The microfluidic chip of claim 1, wherein the volume of said at least one valley of said at least one main channel is between about 1.2 and about 1.8 times of the volume of the at least one reaction chamber connected to said at least one valley.

14. The microfluidic chip of claim 1, wherein the ratio between the narrowest and the widest cross sectional areas in said at least one main channel is between about 0.2 and about 1.

15. The microfluidic chip of claim 1, wherein the ratio between the narrowest and the widest cross sectional areas in said at least one main channel is less than about 1, and wherein the cross sectional area of said at least one peak is smaller than that of said at least one valley.

16. The microfluidic chip of claim 1, wherein said bottom plate comprises between 5 and 100 reaction chambers.

17. The microfluidic chip of claim 1, wherein the thickness of said bottom plate is between about 0.05 mm and about 5 mm.

18. The microfluidic chip of claim 1, wherein the thickness of said cover plate is between about 0.05 mm and about 5 mm.

19. The microfluidic chip of claim 1, wherein the depth of said at least one main channel is between about 40 µm and about 4 mm.

20. The microfluidic chip of claim 1, wherein the depth of said at least one reaction chamber is between about 40 µm and about 4 mm.

21. The microfluidic chip of claim 1, wherein the depth of said at least one linking channel is between about 40 µm and about 4 mm.

22. The microfluidic chip of claim 1, wherein the depth of said at least one buffering chamber is between about 40 µm and about 4 mm.

23. The microfluidic chip of claim 1, wherein said at least one sample inlet port is round, and the size of said at least one sample inlet port matches the size of a standard tip head.

24. A method of analyzing an analyte, comprising:
   1) loading a sample into the at least one main channel of the microfluidic chip of claim 1;
   2) applying a centrifugal force to the microfluidic chip, thereby delivering the sample from the at least one main channel to the at least one reaction chamber;
   3) performing a reaction of the sample in the at least one reaction chamber; and
   4) measuring an indicator of the reaction,
   wherein the indicator indicates the presence, absence, amount, and/or a property of an analyte in the sample.

25. The method of claim 24, wherein the sample is a biological sample.

26. The method of claim 24, wherein the sample is derived from a connective, epithelium, muscle or nerve tissue; a tissue selected from the group consisting of brain, lung, liver, spleen, bone marrow, thymus, heart, lymph, blood, bone, cartilage, pancreas, kidney, gall bladder, stomach, intestine, testis, ovary, uterus, rectum, nervous system, gland, and internal blood vessels; or a body fluid selected from the group consisting of blood, urine, saliva, bone marrow, sperm, an ascitic fluid, serum and plasma.

27. The method of claim 24, which analyzes the presence, absence, amount, and/or a property of a plurality of analytes.

28. A kit, comprising:
   the microfluidic chip of claim 1; and
   one or more reagents for performing a reaction in the microfluidic chip.

29. The kit of claim 28, further comprising a reference indicator of the reaction.

30. The kit of claim 29, wherein the reference indicator comprises a positive and/or a negative reference indicator of the reaction.

31. The kit of claim 28, further comprising an instruction for interpreting a result of the reaction.

32. The kit of claim 28, wherein the reaction is a biological reaction or a chemical reaction.

* * * * *